(12) United States Patent
Mao et al.

(10) Patent No.: US 9,421,182 B2
(45) Date of Patent: Aug. 23, 2016

(54) COCRYSTALS OF DIMETHYL FUMARATE

(71) Applicant: XenoPort, Inc., Santa Clara, CA (US)

(72) Inventors: Chen Mao, Mountain View, CA (US); Scott L. Childs, Atlanta, GA (US); Sami Karaborni, Cupertino, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 14/311,020

(22) Filed: Jun. 20, 2014

(65) Prior Publication Data

US 2014/0378542 A1    Dec. 25, 2014

Related U.S. Application Data

(60) Provisional application No. 61/838,016, filed on Jun. 21, 2013.

(51) Int. Cl.
*A61K 31/225* (2006.01)
*A61K 47/12* (2006.01)
*A61K 31/194* (2006.01)
*C07C 65/05* (2006.01)
*C07C 69/60* (2006.01)

(52) U.S. Cl.
CPC ............ *A61K 31/225* (2013.01); *A61K 31/194* (2013.01); *A61K 47/12* (2013.01); *C07C 65/05* (2013.01); *C07C 69/60* (2013.01); *C07B 2200/13* (2013.01)

(58) Field of Classification Search
CPC ... A61K 47/12; A61K 31/225; A61K 31/194
See application file for complete search history.

(56) References Cited

U.S. PATENT DOCUMENTS

| | | | |
|---|---|---|---|
| 3,139,395 A | 6/1964 | Griffin | |
| 3,336,364 A | 8/1967 | Dill | |
| 4,851,439 A | 7/1989 | Speiser et al. | |
| 4,863,916 A | 9/1989 | Habich et al. | |
| 4,959,389 A | 9/1990 | Speiser et al. | |
| 5,073,641 A | 12/1991 | Bundgaard et al. | |
| 5,145,684 A | 9/1992 | Liversidge et al. | |
| 5,149,695 A | 9/1992 | Speiser et al. | |
| 5,424,332 A | 6/1995 | Speiser et al. | |
| 5,451,667 A | 9/1995 | Speiser et al. | |
| 5,534,250 A | 7/1996 | Klaveness et al. | |
| 6,130,248 A | 10/2000 | Nudelman et al. | |
| 6,277,882 B1 | 8/2001 | Joshi et al. | |
| 6,355,676 B1 | 3/2002 | Joshi et al. | |
| 6,359,003 B1 | 3/2002 | Joshi et al. | |
| 6,379,697 B1 | 4/2002 | Gregoriadis et al. | |
| 6,436,992 B1 | 8/2002 | Joshi et al. | |
| 6,509,376 B1 | 1/2003 | Joshi et al. | |
| 6,613,800 B1 | 9/2003 | Smith | |
| 6,709,868 B2 | 3/2004 | Law et al. | |
| 6,723,508 B2 | 4/2004 | Sprenger et al. | |
| 6,858,750 B2 | 2/2005 | Joshi et al. | |
| 7,157,423 B2 | 1/2007 | Joshi et al. | |
| 7,320,999 B2 | 1/2008 | Joshi et al. | |
| 7,432,240 B2 | 10/2008 | Joshi et al. | |
| 7,612,110 B2 | 11/2009 | Joshi et al. | |
| 7,619,001 B2 | 11/2009 | Joshi et al. | |
| 7,638,118 B2 | 12/2009 | Flachsmann et al. | |
| 7,790,916 B2 | 9/2010 | Joshi et al. | |
| 7,803,840 B2 | 9/2010 | Joshi et al. | |
| 7,906,659 B2 | 3/2011 | Joshi et al. | |
| 7,915,310 B2 | 3/2011 | Joshi et al. | |
| 8,067,467 B2 | 11/2011 | Joshi et al. | |
| 8,148,414 B2 | 4/2012 | Gangakhedkar et al. | |
| 8,399,514 B2 | 3/2013 | Lukashev et al. | |
| 8,524,773 B2 | 9/2013 | Joshi et al. | |
| 8,669,281 B1 | 3/2014 | Zeidan et al. | |
| 8,759,393 B2 | 6/2014 | Joshi et al. | |
| 8,778,991 B2 | 7/2014 | Gangakhedkar et al. | |
| 8,785,443 B2 | 7/2014 | Gangakhedkar et al. | |
| 8,906,420 B2 | 12/2014 | Nilsson et al. | |
| 8,952,006 B2 | 2/2015 | Cundy et al. | |
| 2003/0018072 A1 | 1/2003 | Joshi et al. | |
| 2004/0054001 A1 | 3/2004 | Joshi et al. | |
| 2004/0102525 A1 | 5/2004 | Kozachuk | |
| 2005/0095292 A1 | 5/2005 | Benjamin et al. | |
| 2005/0096369 A1 | 5/2005 | Hoang | |
| 2005/0101779 A1 | 5/2005 | Sagi et al. | |
| 2005/0148664 A1 | 7/2005 | Joshi et al. | |
| 2006/0205659 A1 | 9/2006 | Joshi et al. | |
| 2006/0269925 A1 | 11/2006 | Nunes et al. | |
| 2007/0009475 A1 | 1/2007 | Flachsmann et al. | |
| 2007/0027076 A1 | 2/2007 | Joshi et al. | |
| 2007/0213300 A1 | 9/2007 | Liu et al. | |
| 2007/0231382 A1 | 10/2007 | Karnachi et al. | |
| 2007/0248663 A1 | 10/2007 | Joshi et al. | |
| 2007/0253902 A1 | 11/2007 | Lobb et al. | |

(Continued)

FOREIGN PATENT DOCUMENTS

| | | |
|---|---|---|
| CN | 1616400 | 5/2005 |
| CN | 101318901 A | 12/2008 |
| CN | 101774913 A | 7/2010 |
| DE | 1165586 | 3/1964 |
| DE | 10360869 A1 | 4/2005 |
| EP | 2692344 A1 | 2/2014 |
| GB | 1153927 A | 6/1969 |
| GB | 1404989 A | 9/1975 |
| GB | 2285805 A | 7/1995 |
| JP | S60181047 | 9/1985 |

(Continued)

OTHER PUBLICATIONS

Atreya et al., "NF-κB in inflammatory bowel disease," Journal of Internal Medicine (2008), 263(6), pp. 591-596.

(Continued)

*Primary Examiner* — Yong Chu

(74) *Attorney, Agent, or Firm* — Polsinelli PC

(57) ABSTRACT

Disclosed herein are cocrystals of dimethyl fumarate, which is a prodrug of methyl hydrogen fumarate.

10 Claims, 13 Drawing Sheets

(56) References Cited

U.S. PATENT DOCUMENTS

| | | |
|---|---|---|
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0260755 A1 | 10/2010 | Gammans et al. |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Nilsson et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0284245 A1 | 9/2014 | Karaborni et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0364604 A1 | 12/2014 | Raillard et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |
| 2015/0265707 A1 | 9/2015 | Manthati et al. |

FOREIGN PATENT DOCUMENTS

| | | |
|---|---|---|
| JP | H03294245 | 12/1991 |
| JP | 2001158760 | 6/2001 |
| JP | 2002-027998 A | 1/2002 |
| PL | 153592 | 10/1991 |
| WO | WO 96/36613 | 11/1996 |
| WO | WO 98/29114 | 7/1998 |
| WO | WO 98/52549 | 11/1998 |
| WO | 99/21559 | 5/1999 |
| WO | WO 99/49858 | 10/1999 |
| WO | WO 99/51191 A1 | 10/1999 |
| WO | WO 99/62973 A1 | 12/1999 |
| WO | WO 00/10560 A1 | 3/2000 |
| WO | WO 00/12072 A2 | 3/2000 |
| WO | WO 02/055063 | 7/2002 |
| WO | WO 02/055066 | 7/2002 |
| WO | WO 02/055067 | 7/2002 |
| WO | WO 03/087174 | 10/2003 |
| WO | 2005/023241 A1 | 3/2005 |
| WO | WO 2005/027899 | 3/2005 |
| WO | WO 2006/037342 | 4/2006 |
| WO | WO 2006/050730 | 5/2006 |
| WO | WO 2006/122652 | 11/2006 |
| WO | WO 2007/006307 | 1/2007 |
| WO | WO 2007/006308 | 1/2007 |
| WO | WO 2007/042034 | 4/2007 |
| WO | WO 2007/042035 | 4/2007 |
| WO | WO 2008/096271 | 8/2008 |
| WO | WO 2008/097596 | 8/2008 |
| WO | WO 2010/022177 | 2/2010 |
| WO | WO 2010/079221 | 7/2010 |
| WO | WO 2010/079222 | 7/2010 |
| WO | WO 2010/126605 | 11/2010 |
| WO | WO 2011/080344 | 7/2011 |
| WO | 2011/100589 | 8/2011 |
| WO | WO 2012/162669 | 11/2012 |
| WO | WO 2012/170923 | 12/2012 |
| WO | WO 2013/022882 | 2/2013 |
| WO | WO 2013/076216 | 5/2013 |
| WO | WO 2013/119677 | 8/2013 |
| WO | WO 2013/119791 | 8/2013 |
| WO | 2014/020156 | 2/2014 |
| WO | WO 2014/031894 | 2/2014 |
| WO | WO 2014/031897 | 2/2014 |
| WO | WO 2014/071371 | 5/2014 |
| WO | WO 2014/096425 | 6/2014 |
| WO | WO 2014/100728 | 6/2014 |
| WO | WO 2014/190056 | 11/2014 |
| WO | WO 2015/028472 | 3/2015 |
| WO | WO 2015/028473 | 3/2015 |

OTHER PUBLICATIONS

Barnes, "Mediators of chronic obstructive pulmonary disease," Pharmacological Reviews (2004), 56(4), pp. 515-548.

Blandini, et al., "Glutamate and Parkinson's disease," Molecular Neurobiology (1996), 12(1), pp. 73-94.

Camandola et al., "NF-κB as a therapeutic target in neurodegenerative diseases," Expert Opinion Therapeutic Targets (2007), 11(2), pp. 123-132.

Dawson et al., "Bioequivalence of BG-12 (Dimethyl Fumarate) Administered as a Single 240 mg Capsule and Two 120 mg Capsules: Findings from a Randomized, Two-period Crossover Study", Poster P913 presented at the 28th Congress of the European Committee for Treatment and Research in Multiple Sclerosis, Oct. 10-13, 2012, Lyon France, 1 page.

Etter et al., "The Use of Cocrystallization as a Method of studying Hydrogen Bond Preferences of 2-Aminopyrimidine," Journal of the Chemical Society (1990), No. 8, pp. 589-591.

Etter et al., "Graph Set Analysis of Hydrobgen-Bond Patterns in Organic Crystals," Acta Crystallogr., Sect. B, Struct. Sci. (1990), B46, pp. 256-262.

Etter et al., "Hydrogen Bond Directed Cocrystallization and Molecular Recognition Properties of Diarylureas," Journal of the Chemical Society (1990), No. 112, pp. 8415-8426.

(56) References Cited

OTHER PUBLICATIONS

Gorbitz et al., "On the inclusion of solvent molecules in the crystal structures of organic compounds," Acta Cryst. (2000), B56, pp. 526-534.
Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.
Loewe et al., "Dimethylfumarate inhibits TNF-induced nuclear entry of NF-κB/p65 in human endothelial cells," The Journal of Immunology (2002), 168, pp. 4781-4787.
Martin, "Molecular basis of the neurodegenerative disorders," The New England Journal of Medicine (1999), 340 (25), pp. 1970-1980.
Meissner et al., "Dimethyl fumarate—only an anti-psoriatic medication?", Journal Der Deutschen Demrmatologischen Gesellschaft (2012), vol. 10, pp. 793-801.
Mrowietz, et al., "Dimethylfumarate for psoriasis: more than a dietary curiosity," Trends in Molecular Medicine (2005), 11(1), pp. 43-48.
Mrowietz et al., "Treatment of severe psoriasis with fumaric acid esters: scientific background and guidelines for therapeutic use," British Journal of Dermatology (1999), 141, pp. 424-429.
Rowland et al., "Amyotrophic lateral sclerosis," The New England Journal of Medicine (2001), 344(22), pp. 1688-1700.
Schimrigk, et al., "Oral fumaric acid esters for the treatment of active multiple sclerosis: an open-label, baseline-controlled pilot study," European Journal of Neurology (2006), vol. 13, pp. 604-610.
Shan et al., "The role of cocrystals in pharmaceutical science," Drug Discovery Today (2008), 13(9/10), pp. 440-446.
Sheikh, et al., "Safety Tolerability and Pharmacokinetics of BG-12 Administered with and without Aspirin, Key Findings from a Randomized, Double-blind, placebo-controlled trial in healthy volunteers", Poster P04.136 presented at the 64th Annual Meeting of the American Academy of Neurology, Apr. 21-28, 2012, New Orleans, LA, 1 page.
Tracey et al., "Tumor necrosis factor antagonist mechanisms of action: a comprehensive review," Pharmacology & Therapeutics (2008), 117, pp. 244-279.
Virley, "Developing therapeutics for the treatment of multiple sclerosis," NeuroRx: The Journal of the American Society for Experimental NeuroTherapeutics (2005), vol. 2, pp. 638-649.
Vishweshwar et al., "Pharmaceutical Co-Crystals," Journal of Pharmaceutical Sciences (2006), 95(3), pp. 499-516.
Wakkee et al., "Drug evaluation: BG-12, an immunomodulary dimethylfumarate," Current Opinion in Investigational Drugs (2007), 8(11), pp. 955-962.
Wingerchuk et al., "Multiple sclerosis: current pathophysiological concepts," Laboratory Investigation (2001), 81(3), pp. 263-281.
Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.
Altmeyer et al., Antipsoriatic effect of fumaric acid derivatives, J. Amer. Acad. Derm. (1994), 30(6): 977-981.
Altschul et al., "Gapped BLAST and PSI-BLAST: a new generation of protein database search programs," Nucleic Acids Research, 1997, vol. 25, No. 17, pp. 3389-3402.
Ashe, Learning and memory in transgenic mice modeling Alzheimer's disease. Learning & Memory (2001), 8, 301-308.
Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>; Sep. 24, 2003; 2 pages.
Author Unknown, BG 00012, BG 12/oral fumarate, FAG-201, second-generation fumarate derivative—Fumapharm/Biogen Idec, Drugs RD (2005), 6(4): 229-230.

Bar-Or et al., "Clinical efficacy of BG-12 (dimethyl fumarate) in patients with relapsing-remitting multiple sclerosis: subgroup analyses of the Define study," J. Neurol, 2013, vol. 260, pp. 2297-2305.
Bardgett et al., NMDA receptor blockade and hippocampal neuronal loss impair fear conditioning and position habit reversal in C57Bl/6 mice. Brain Res Bull (2003), 60, 131-142.
Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.
Benoit et al., Etude Clinique de L'ester B-Morpholinoethylique de L'Acide Niflumique en Stomatologie Infantile, Rev. Odontostomatol Midi Fr. (1975), 4: 249-261.
Bertone, "Prevalence of Gastric Ulcers in Elite, Heavy Use Western Performance Horses," AAEP Proceedings (2000). 46: 256-259.
Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. J Pharmacol Expt'l Therapeutics (2008), 324(3), 938-947.
Blad, et al., "Biological and Pharmacological Roles of HCA Receptors", Advances in Pharmacology, 2011, 62: 219-250.
Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.
Brewer, et al., "Fumaric acid esters in the management of severe psoriasis", Clinical Experimental Dermatology, 2007, 32: 246-249.
Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.
Bruhn et al., "Concordance between enzyme activity and genotype of glutathione S-transferase theta (GSTT1)," Biochemical Pharmacology, 1998, vol. 56, pp. 1189-1193.
Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.
Bundgaard et al., Glycolamide esters as a novel biolabile prodrug type for non-steroidal anti-inflammatory carboxylic acid drugs, Int. J. Pharm. (1988) 43: 101-110.
Büyükcoskun, Central Effects of Glucagon-like Peptide-1 on Cold Restraint Stress-induced Gastric Mucosal Lesions, Turk J. Gastroenterol (2007), 18(3): 150-156.
Büyükcoskun, Role of Intracerebroventricular Vasopressin in the Development of Stress-Induced Gastric Lesions in Rats, Physiol. Res. (1999), 48: 451-455.
Caira, "Crystalline Polymorphism of Organic Compounds," Topics in Current Chemistry, Springer, Berlin, DE (1998), vol. 198, pp. 163-208.
Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.
Cavarra et al., Effects of cigarette smoke in mice with different levels of α1-proteinase inhibitor and sensitivity to oxidants. Am J Respir Crit Care Med (2001), 164, 886-890.
Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.
Chaudhary et al., "Enhancement of solubilization and bioavailability of poorly soluble drugs by physical and chemical modifications: A recent review," Journal of Advanced Pharmacy Education & Research (2012), 2(1), pp. 32-67.
Chen et al., "Nanonization strategies for poorly water-soluble drugs," Drug Discovery Today, 2010, pp. 1-7.
Cockcroft et al., Bronchial reactivity to inhaled histamine: a method and clinical survey. Clin Allergy (1977), 7, 235-243.

(56) References Cited

OTHER PUBLICATIONS

Cross, et al. Dimethyl Fumarate, an Immune Modulator and Inducer of the Antioxidant Response, Suppresses HIV Replication and Macrophage-Mediated Neurotoxicity: A Novel Candidate for HIV Neuroprotection. The Journal of Immunology, (2011), 187(10): 5015-5025.
D'Acquisto et al., Inhibition of nuclear factor kappa B (NF-κB): an emerging theme in anti-inflammatory therapies. Molecular Interventions (2002), 2(1), 22-35.
Damasio; "Alzheimer's Disease and Related Dementias;" Cecil Textbook of Medicine; 1996; 20th Edition, vol. 2; pp. 1992-1996.
De Jong et al., Selective stimulation of T helper 2 cytokine responses by the anti-psoriasis agent monomethylfunarate, Eur. J. Immunol. (1996), 26: 2067-2074.
Dibbert, et al.,: "Detection of fumarate-glutathione adducts in the portal vein blood of rats: Evidence for rapid dimethyl fumarate metabolism", Archives of Dermatological Research 2013 Springer Verlag Deu, vol. 305, No. 5, Jul. 2013, pp. 447-451.
Dymicky, Preparation of Monomethyl Fumarate, Organic Preparations and Procedures International, vol. 15 No. 4 (1983), pp. 233-238.
Eberle, et al. Fumaric Acid Esters in Severe Ulcerative Necrobiosis Lipoidica: A Case Report and Evaluation of Current Therapies. Acta Dermato-Venereologica (2010) 90(1): 104-106.
Ellrichmann et al., Efficacy of fumaric acid esters in the R6/2 and YAC128 models of Huntington's disease, PLOS One (2011), 6(1): 11 pages.
Eugster et al., Superantigen overcomes resistance of IL-6 deficient mice towards MOG-induced EAE by a TNFR1 controlled pathway. Eur J Immunol (2001), 31, 2302-2312.
European Commission Health & Consumer Protection Directorate-General, Report of the scientific committee on animal nutrition on the safety of fumaric acid, adopted Jan. 22, 2003: 18 pages.
Feinstein et al., Anti-inflammatory and prometabolic effects of BG-12 in glial cells, 26th Congress Eur. Cmtee. Treat. Res. Mult. Scler. (2010), poster: 1 page.
Fits et al., Imiquimod-Induced Psoriasis-Like Skin Inflammation in Mice is Mediated via the IL-23/IL-17 Axis, J. Immunol. (2009), 182: 5836-5845.
Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.
Fox et al., Baseline characteristics of patients in a randomized, multicenter, placebo-controlled and active comparator trial evaluating efficacy and safety of BG-12 in relapsing-remitting multiple sclerosis: the Confirm trial, 62nd Ann Mtg. Amer. Acad. Neurol. (2010), poster, 2 pages.
Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.
Frycak et al., Evidence of covalent interaction of fumaric acid esters with sulfhydryl groups in peptides, J. Mass. Spectrom. (2005), 40: 1309-1318.
Gadad et al., Synthesis, spectral studies and anti-inflammatory activity of glycolamide esters of niflumic acid as potential prodrugs, Arzneim Forsch Drug Res. (2002), 52(11): 817-821.
Gambichler, et al. Clearance of Necrobiosis lipoidica with Fumaric Acid Esters. Dermatology (2003), 207(4): 422-424.
Gesser et al., Dimethylfumarate specifically inhibits the mitogen and stress-activated kinases 1 and 2 (MSK1/2): Possible role for its anti-psoriatic effect. J Investigative Dermatology (2007), 127, 2129-2137.
Goke et al., Effect of a Specific Serine Protease Inhibitor on the Rat Pancreas: Systemic Administration of Camostate and Exocrine Pancreatic Secretion, Digestion (1984) 30: 171-178.

Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.
Gold et al., Baseline characteristics of patients in the DEFINE trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.
Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.
Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011, pp. 2291-2303.
Griffin, et al., The Chemistry of Photodimers of Maleic and Fumaric Acid Derivatives. I. Dimethyl Fumarate Dimer; J. Am. Chem. Soc. (1961), 83: pp. 2725-2728.
Grigorian et al., Control of T-cell mediated autoimmunity by metabolite flux to N-glycan biosynthesis, J. Bio. Chem. (2007), 282(27): 20027-20035.
Guenther, et al., Macular Exanthema Due to Fumaric Acid Esters. Annals of Pharmacotherapy (2003), 37(2): 234-236.
Gurney et al., Motor neuron degeneration in mice that express a human Cu,Zn superoxide dismutase mutation. Science (1994), 264, 1772-1775.
Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.
Heiligenhaus, et al. Influence of dimethylfumarate on experimental HSV-1 necrotizing keratitis. Graefe's Archive for Clinical and Experimental Ophthalmology (2004), 242(10): 870-877.
Heiligenhaus, et al. Improvement of herpetic stromal keratitis with fumaric acid derivate is associated with systemic induction of T helper 2 cytokines. Clinical and Experimental Immunology (2011), 142(1): 180-187.
Hiraku et al., Absorption and Excretion of Camostat Orally Administered to Male Rabbit and Healthy Subject, Iyakuhin Kenkyu (1982) 13(3): 756-765.
Hoefnagel, et al., "Long-term safety aspects of systemic therapy with fumaric acid esters in severe psoriasis", British Journal of Dermatology, 2003, 149: 363-369.
Horig et al., From bench to clinic and back: Perspective on the 1st IQPC Translational Research Conference, J. Transl. Med. (2004), 2(44), 8 pages.
Hoxtermann et al., Fumaric acid esters suppress peripheral CD4- and CD8-positive lymphocytes in psoriasis, Dermatology (1998), 196: 223-230.
Hurd et al., Vinylation and the Formation of Acylals:, J. Am. Chem. Soc.; vol. 78; Jan. 5, 1956; pp. 104-106.
Iyer et al., Synthesis of iodoalkylacylates and their use in the preparation of S-alkyl phosphorothiolates. Synth Commun (1995), 25(18), 2739-2749.
Jamil, et al., "Studies of Photostability of Reserpine in Parenteral Solutions," Die Pharmazie (1983), 38: pp. 467-469.
Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.
Jurjus et al., Animal models of inflammatory bowel disease. J Pharmacol Toxicol Methods (2004), 50, 81-92.
Kappos et al., Efficacy and safety of oral fumarate in patients relapsing-remitting multiple sclerosis: a multicentre, randomised, double-blind, placebo controlled phase IIb study, Lancet (2008), 372: 1463-1472.
Kamimura et al., "Stereoselective formation of optically active 2-oxy-1,3- oxazolidin-4-ones from chiral O-acylmandelamides or lactamides", Tetrahedron 58, 2002, 8763-8770.
Khan et al., Synthesis and biological evaluation of glycolamide esters as potential prodrugs of some non-steroidal anti-inflammatory drugs, Ind. J. Chem. (2002) 41B: 2172-2175.

(56) References Cited

OTHER PUBLICATIONS

Killestein, et al., "Oral treatment for multiple sclerosis," Lancet Neurology, Lancet Publishing Group, London, GB, vol. 10, No. 11, Nov. 2011, pp. 1026-1034.
Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).
Kreuter et al., Fumaric acid esters in necrobiosis lipoidica: results of a prospective noncontrolled study. British Journal of Dermatology (2005) 153(4): 802-807.
Layzer; "Section Five—Degenerative Diseases of the Nervous System"; Cecil Textbook of Medicine; 1996; 20th Edition, vol. 2; pp. 2050-2057.
Lee et al., Spotlight on fumarates, Int. MS J. (2008), 15: 12-18.
Lehmann et al., Fumaric acid esters are potent immunosuppressants: inhibition of acute and chronic rejection in rat kidney transplantation models by methyl hydrogen fumarate. Arch Dermatol Res (2002), 294, 399-404.
Lehmann et al., Dimethylfumarate induces immunosuppression via glutathione depletion and subsequent induction of heme oxygenase 1. J Investigative Dermatology (2007), 127, 835-845.
Lei et al., "Novel Technology of Dimethyl Fumarate Synthesis," Ziyuan Kaifa Yu Shichang (2011), 27(9), pp. 787-789.
Linker et al., Identification and development of new therapeutics for multiple sclerosis, Treds. Pharm. Sci. (2008), DOI 10.1016/j.tips. 2008.07.012, 8 pages.
Linker et al., Fumaric acid esters exert neuroprotective effects in neuroinflammation via activation of the Nrf2 antioxidant pathway, Brain (2011), 134: 678-692.
Litjens e al., Monomethylfumarate affects polarization of monocyte-derived dendritic cells resulting in down-regulated Th1 lymphocyte responses, Eur. J. Immunol. (2004), 34: 565-575.
Litjens et al., Pharmacokinetics of oral fumarates in healthy subjects, Br. J. Clin. Pharmacol. (2004), 58(4): 429-432.
Litjens et al., Effects of monomethylfumarate on dendritic cell differentiation, Br. J. Dermatol. (2006), 154: 211-217.
Loewe et al., Dimethylfumarate impairs melanoma growth in metastasis, Cancer Res. (2006), 66(24): 11888-11896.
Lopez-Diego et al., Novel therapeutic strategies for multiple sclerosis—a multifaceted adversary, Nat. Review. Drug Disc. (2008), 7:909-925.
Los et al., Nuevos Estered De Acidos Anilinonicotinicos Y N-Fenilantranilicos Sustituidos, II Farmaco—Ed. Sc. (1980), 36(5): 372-85.
Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.
Mandhane, et al., Adenosine A2 receptors modulate haloperidol-induced catalepsy in rats. Eur. J. Pharmacol (1997), 328, 135-141.
Martorana et al., Roflumilast fully prevents emphysema in mice chronically exposed to cigarette smoke. Am J Respir Crit Care Med (2005), 172, 848-853.
Menter et al., Guidelines of care for the management of psoriasis and psoriatic arthritis, J. Am. Acad. Dermatol. (2009), doi:10.1016/j.jaad.2009.03.027, 35 pages.
Merisko-Liversidge et al., "Nanosizing: a formulation approach for poorly-water-soluble compounds," European Journal of Pharmaceutical Sciences, 18 (2003), pp. 113-120.
Miller et al., Experimental Autoimmune Encephalomyelitis in the Mouse, Current Protocols in Immunology (2007), Supp. 78: 15.1.1-15.1.18.
Milo, et al., "Combination therapy in multiple sclerosis", Journal of Neuroimmunology, vol. 231, No. 1, 2011, pp. 23-31.
Mosmann et al., TH1 and TH2 cells: different patterns of lymphokine secretion lead to different functional properties, Ann. Rev. Immunol. (1989), 7: 145-73.
Mrowietz, et al., "Treatment of Psoriasis with Fumaric Acid Esters: Results of a prospective Multicenter Study," British Journal of Dermatology (1998), 138: 456-460.
Mrowietz et al., Treatment of psoriasis with fumaric acid esters (Fumaderm®), JDDG (2007), DOI: 10.1111/j.1610-0387.2007.06346.x, 2 pages.
Muller et al., "High-performance liquid chromatography/fluorescence detection of S-methylglutathione formed by glutathione-S-transferase T1 in vitro," Arch Toxicol, 2001, vol. 74, pp. 760-767.
Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.
Naldi et al., Psoriasis (chronic plaque), Clin. Evid. (2009), 1(1706): 50 pages.
Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.
Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.
Nibbering et al., Intracellular signalling by binding sites for the antipsoriatic agent monomethylfumarate on human granulocytes, Br. J. Dermatol. (1997), 137: 65-75.
Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, Apr. 1988, pp. 285-298.
Offermans, The nicotinic acid receptor GPR109A (HM74A or PUMA-G) as a new therapeutic agent, Trends Pharm. Sci. (2006), 27(7): 384-390.
O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.
Panagiotou et al., "Form Nanoparticles via Controlled Crystallization," Chemical Engineering Progress; Oct. 2008, 104, 10, pp. 33-39.
Pathak et al., "Supercritical fluid technology for enhanced drug delivery," Expert Opin. Drug Deliv. (2005) 2(4):747-761.
Peeters et al., Fumaric acid therapy for psoriatic arthritis. A randomized, double-blind, placebo-controlled study, Br. J. Rheumatol. (1992), 31(7): 502-504.
Pemble et al., "Human glutathione S-transferase Theta (GSTT1): cDNA cloning and the characterization of a genetic polymorphism," Biochem. J., 1994, vol. 300, pp. 271-276.
Rantanen, The cause of the Chinese sofa/chair dermatitis epidemic is likely to be contact allergy to dimethylfumarate, a novel potent contact sensitizer, Br. J. Dermatol. (2008), 159: 218-221.
Reddingius, Bioanalysis and pharmacokinetics of fumarates in humans, Ph.D. dissertation ETH No. 12199, Swiss Fed. Inst. Tech. Zurich (1997), 82 pages.
Reich et al., Efficacy and safety of fumaric acid esters in the long-term treatment of psoriasis — a retrospective study (Future), JDDG (2009), DOI: 10.1111/j.1610-0387.2009.07120.x, 8 pages.
Richman et al., Nicotinic acid receptor agonists differentially activate downstream effectors, J. Bio. Chem. (2007), 282(25): 18028-18036.
Roll et al., Use of fumaric acid esters in psoriasis, Indian J. Dermatol. Ven. Lep. (2007), 73: 133-137.
Rostami-Yazdi, et al., "Detection of Metabolites of Fumaric Acid Esters in Human Urine: Implications for their mode of action", Journal of Investigative Dermatology, 2008, pp. 1-3,.
Rostami-Yazdi et al., Pharmacokinetics of antipsoriatic fumaric acid esters in psoriasis patients, Arch. Dermatol. Res. (2010), 302: 531-538.
Rubant et al., Dimethylfumarate reduces leukocyte rolling in vivo through modulation of adhesion molecule expression, J. Invest. Dermatol. (2007), 128: 326-331.

(56) References Cited

OTHER PUBLICATIONS

Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.

Schafer et al., "Failure is an option: learning from unsuccessful proof-of-concept trials", Drug Discovery Today, vol. 13, Nos. 21/22; Nov. 2008; pp. 913-916.

Schilling, et al., "Fumaric acid esters are effective in chronic experimental autoimmune encephalomyelitis and suppress macrophage infiltration", Clinical and Experimental Immunology, 2006, 145: pp. 101-107.

Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006, pp. 333-342.

Seder et al., Acquisition of lymphokine-producing phenotype by CD4+ T-cells, Ann. Rev. Immunol. (1994), 12: 635-73.

Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.

Soelberg Sorensen et al., Oral fumarate for relapsing-remitting multiple sclerosis, Lancet (2008), 372: 1447-1448.

Spatz, et al., Methyl Hydrogen Fumarate, Journal of Organic Chemistry, 1958, 23 (10), 1559-1560.

Spencer et al., Induction of glutathione transferases and NAD(P)H: quinone reductase by fumaric acid derivatives in rodent cells and tissues, Cancer Res. (1990), 50: 7871-7875.

Spencer, "Tecfidera: an approach for repurposing," Pharmaceutical Patent Analyst, 2014, vol. 3(2), pp. 183-198.

Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.

Steckel et al., "The extrusion and speronization of chitosan," Pharmaceutical Technology Europe, <http://www.pharmtech.com/extrusion-and-spheronization-chitosan>, published Jul. 2, 2007, pp. 1-12.

Stoof et al., The antipsoriatic drug dimethylfumarate strongly suppresses chemokine production in human keratinocytes and peripheral blood mononuclear cells, Br. J. Dermatol. (2001), 144: 1114-1120.

Tabruyn et al., NF-κB: a new player in angiostatic therapy. Angiogenesis (2008), 11, 101-106.

Talath et al., Stability studies of some glycolamide ester prodrugs of niflumic acid in aqueous buffers and human plasma by HPLC with UV detection, Arz. Forsch Drug Res. (2006), 56(9): 631-639.

Talath et al., Synthesis, stability studies, anti-inflammatory activity and ulcerogenicity of morpholinoalkyl ester prodrugs of niflumic acid, Arz. Forsch Drug Res. (2006), 56(11): 744-752.

Tang et al., The psoriasis drug monomethylfumarate is a potent nicotinic acid receptor agonist, Biochem. Biophys. Res. Comm. (2008), doi:10.1016/j.bbrc.2008.08.041, 4 pages.

Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.

Thomson et al., FK 506: a novel immunosuppressant for treatment of autoimmune disease: rationale and preliminary clinical experience at the University of Pittsburgh, Springer Semin. Immunopathol. (1993), 14(4): 323-344.

Treumer et al., Dimethylfumarate is a potent inducer of apoptosis in human T cells. J Invest Dermatol (2003), 121, 1383-1388.

Van Schoor et al., Effect of inhaled fluticasone on bronchial responsiveness to neurokinin A in asthma. Eur Respir J (2002), 19, 997-1002.

Van Schoor et al., The effect of the NK2 tachykinin receptor antagonist SR 48968 (saredutant) on neurokinin A-induced bronchoconstriction in asthmatics, Eur Respir J (1998) 12: 17-23.

Vandermeeren et al., Dimethylfumarate is an inhibitor of cytokine-induced E-selectin, VCAM-1, and ICAM-1 expression in human endothelial cells. Biochem Biophys Res Commun (1997), 234, 19-23.

Villegas et al., A new flavonoid derivative, dosmalfate, attenuates the development of dextran sulphate sodium-induced colitis in mice. Int'l Immunopharmacol (2003), 3, 1731-1741.

Wadhwa et al., Glycolamide esters of 6-methoxy-2-naphthylacetic acid as potential prodrugs—Synthetic and spectral studies, Ind. J. Chem. (1995), 34B: 408-415.

Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.

Wang, et al., Evidence-Based Treatment of Chronic Leg Ulcers in A Patient with Necrobiosis Lipoidica Deabeticorum. Chinese Journal of Evidence-Based Medicine (2007), 7(11): 830-835.

Weber et al., Synthesis, In Vitro Skin Permeation Studies, and PLS-Analysis of New Naproxen Derivatives, Pharm. Res. (2001) 18(5): 600-607.

Weber et al., Treatment of disseminated granuloma annulare with low-dose fumaric acid, Acta Derm. Venereol. (2009), 89: 295-298.

Werdenberg et al., Presystemic metabolism and intestinal absorption of antipsoriatic fumaric acid esters, Biopharm. Drug. Dispos. (2003), 24: 259-273.

Whiteley et al., Models of Inflammation: Measuring Gastrointestinal Ulceration in the Rat, Curr. Protocol. Pharm. (1998): 10.2.1-10.2.4.

Winkler, et al., Oxidative damage and age-related macular degeneration. Molecular vision, (1999), 5:32, 11 pages.

Woodworth et al., Oral BG-12 in combination with interferon beta or glatiramer acetate: pharmacokinetics, safety and tolerability, 26th Congress Eur. Cmtee. Treat. Res. Mult. Scler. (2010), poster: 1 page.

Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.

Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.

XenoPort, Inc., XenoPort announces presentation of preclinical data for novel fumarate analog XP23829 at ECTRIMS, Press Release dated Oct. 13, 2010, 3 pages.

Yamada et al., "Synthesis and Polymerization of Unsaturated Dibasic Acid Derivatives," Yuki Gosei Kagaku Kyokaishi (1965), 23(2), 19 pages.

Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.

Yazdi et al., Fumaric acid esters. Clinics Dermatology (2008), 26, 522-526.

Zhang et al., "Synthesis of Dimethyl Fumarate with Orthogonal Test," Jingxi Huagong Zhongjianti (2006), 36(6), pp. 71-72.

Zhao et al., "Synthesis and antimicrobial active of monomethyl fumarate," Shipin Gongye Keji (2008), 29(6), pp. 259-262.

Zheng et al., "Improved Preparation of Monomethyl Fumarate," Huaxue Shijie (2004), 45(4), pp. 207-208, 217.

Zhu et al., Inhibition of dendritic cell differentiation by fumaric acid esters, J. Invest. Dermatol. (2001), 116: 203-208.

U.S. Appl. No. 14/661,698, filed Mar. 18, 2015, Cundy.

U.S. Appl. No. 14/663,649, filed Mar. 20, 2015, Manthati et al.

U.S. Appl. No. 14/990,582, filed Jan. 7, 2016, Karaborni et al.

O'Donnell et al., "Remington the Science and Practice of Pharmacy" 21st Edition, 2005, Chapter 52, pp. 1025-1036.

(56) References Cited

OTHER PUBLICATIONS

Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pp.

Ivanisevic et al., "Uses of X-Ray Powder Diffraction in the Pharmaceutical Industry," Pharmaceutical Formulation & Quality, 32 (2011), pp. 30-33.

Gogas et al., "Comparison of the efficacy and tolerability of a novel methyl hydrogen fumarate prodrug with dimethyl fumarate in rodent EAE and GI irritation models," Multiple Sclerosis, 2010, vol. 16, No. 10 Supplement, pp. S230-S231.

General pharmaceutics (5th edition), 1997, 5 pages, published in Japan.

Tammara et al., "Morpholinoalkyl Ester Prodrugs of Diclofenac: Synthesis, In Vitro and In Vivo Evaluation," Journal of Pharmaceutical Scienecs, 1994 vol. 83, No. 5, pp. 644-648.

General pharmaceutics (5th edition) with partial translation of pp. 208-209, 1997, 5 pages, published in Japan.

Compound (CAS RN 473669-27-1) entered STN chemical database on Nov. 15, 2002 by Ambinter, 4 pp.

COCRYSTALS OF DIMETHYL FUMARATE

CROSS-REFERENCE

This application claims the benefit under 35 U.S.C. §119(e) of U.S. Provisional Application Ser. No. 61/838,016, filed Jun. 21, 2013, and entitled "Cocrystals of Dimethyl Fumarate," which is incorporated by reference in its entirety.

FIELD

Disclosed herein are novel cocrystalline forms of dimethyl fumarate.

BACKGROUND

Dimethyl fumarate refers to the dimethyl ester of fumaric acid. The compound has a molecular weight of 144.13 daltons and the following chemical structure:

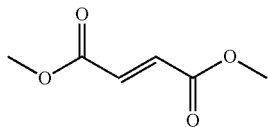

This compound is also known by the names Dimethyl (E)-butenedioate (IUPAC), trans-1,2-Ethylenedicarboxylic acid dimethyl ester and (E)-2-Butenedioic acid dimethyl ester. The compound is also referred to by the acronym DMF. DMF can be synthesized according to the methods described in Chinese Patent Publication CN 101318901A, the disclosures of which are incorporated herein by reference. The compound in crystalline form has a disclosed melting point of between 102° C. and 105° C. Dimethyl fumarate is rapidly metabolized in vivo to monomethyl fumarate (MMF), and hence DMF is considered to be a prodrug of MMF.

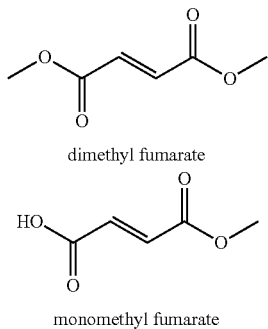

dimethyl fumarate monomethyl fumarate

Fumaderm®, an enteric coated tablet containing a mixture of salts of monoethyl fumarate and dimethyl fumarate, was approved in Germany in 1994 for the treatment of psoriasis. Fumaderm® is dosed three times per day with 1-2 grams/day administered for the treatment of psoriasis.

Tecfidera™, formerly called BG-12, is a delayed release (i.e., a capsule containing enteric-coated minitablets) oral dosage form of dimethyl fumarate. Tecfidera™ (dimethyl fumarate) was approved in the USA in 2013, and is dosed two times per day with 480 mg/day administered for the treatment of multiple sclerosis. Details concerning the clinical testing of BG-12 are disclosed in Sheikh et al., Safety Tolerability and Pharmacokinetics of BG-12 Administered with and without Aspirin, Key Findings from a Randomized, Double-blind, Placebo-controlled Trial in Healthy Volunteers, Poster PO4.136 presented at the 64th Annual Meeting of the American Academy of Neurology, Apr. 21-28, 2012, New Orleans, La.; Dawson et al., Bioequivalence of BG-12 (Dimethyl Fumarate) Administered as a Single 240 mg Capsule and Two 120 mg Capsules: Findings from a Randomized, Two-period Crossover Study, Poster P913 presented at the 28th Congress of the European Committee for Treatment and Research in Multiple Sclerosis, Oct. 10-13, 2012, Lyon, France; and Woodworth et al., Pharmacokinetics of Oral BG-12 Alone Compared with BG-12 and Interferon β-1a or Glatiramer Acetate Administered Together, Studied in Health Volunteers, Poster PO4.207 presented at the 62nd Annual Meeting of the American Academy of Neurology, Apr. 10-17, 2010, Toronto, Ontario, Canada.

Cocrystals are crystals that contain two or more non-identical molecules that form a crystalline structure. The intermolecular interactions between the non-identical molecules in the resulting crystal structures can result in physical and chemical properties that differ from the properties of the individual components. Such properties can include, for example, melting point, solubility, chemical stability, mechanical properties and others. Examples of cocrystals may be found in the Cambridge Structural Database and in Etter, et al., "The use of cocrystallization as a method of studying hydrogen bond preferences of 2-aminopyridine" J. Chem. Soc., Chem. Commun. (1990), 589-591; Etter, et al., "Graph-set analysis of hydrogen-bond patterns in organic crystals" Acta Crystallogr., Sect. B, Struct. Sci. (1990), B46: 256-262; and Etter, et al., "Hydrogen bond directed cocrystallization and molecular recognition properties of diarylgentisic acids" J. Am. Chem. Soc. (1990), 112: 8415-8426. Additional information relating to cocrystals can be found in: Carl Henrik Gorbotz and Hans-Petter Hersleth, "On the inclusion of solvent molecules in the crystal structures of organic compounds"; Acta Cryst. (2000), B56: 625-534; and Senthil Kumar, et al., "Molecular Complexes of Some Mono- and Dicarboxylic Acids with trans-1,4,-Dithiane-1,4-dioxide" American Chemical Society, Crystal Growth & Design (2002), 2(4): 313-318.

SUMMARY

The present disclosure describes cocrystalline forms of dimethyl fumarate having improved physicochemical properties that may be used in pharmaceutical processing and in pharmaceutical compositions and therapeutic methods of treatment.

In a first aspect, a cocrystal of dimethyl fumarate and gentisic acid, pharmaceutical compositions containing the cocrystal, and methods of administering the cocrystal to a patient for treating a disease, are provided. In a particular embodiment, the cocrystal has dimethyl fumarate to gentisic acid molar ratio of about 1:2.

In a second aspect, a cocrystal of dimethyl fumarate and (+)-camphoric acid, pharmaceutical compositions containing the cocrystal, and methods of administering the cocrystal to a patient for treating a disease, are provided.

In one particular embodiment, the cocrystal of dimethyl fumarate and (+)-camphoric acid is of Form 1, which is isolated by a solution method as described herein.

In another particular embodiment, the cocrystal of dimethyl fumarate and (+)-camphoric acid is of Form 2, which is isolated by a milling method as described herein. In a particular embodiment, the cocrystal has dimethyl fumarate to (+)-camphoric acid molar ratio of about 1:4.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which forms a part of this disclosure.

BRIEF DESCRIPTION OF THE DRAWINGS

In addition to the exemplary aspects and embodiments described above, further aspects and embodiments will become apparent by reference to the drawings and by study of the following descriptions.

DETAILED DESCRIPTION

Definitions

Figure 1:
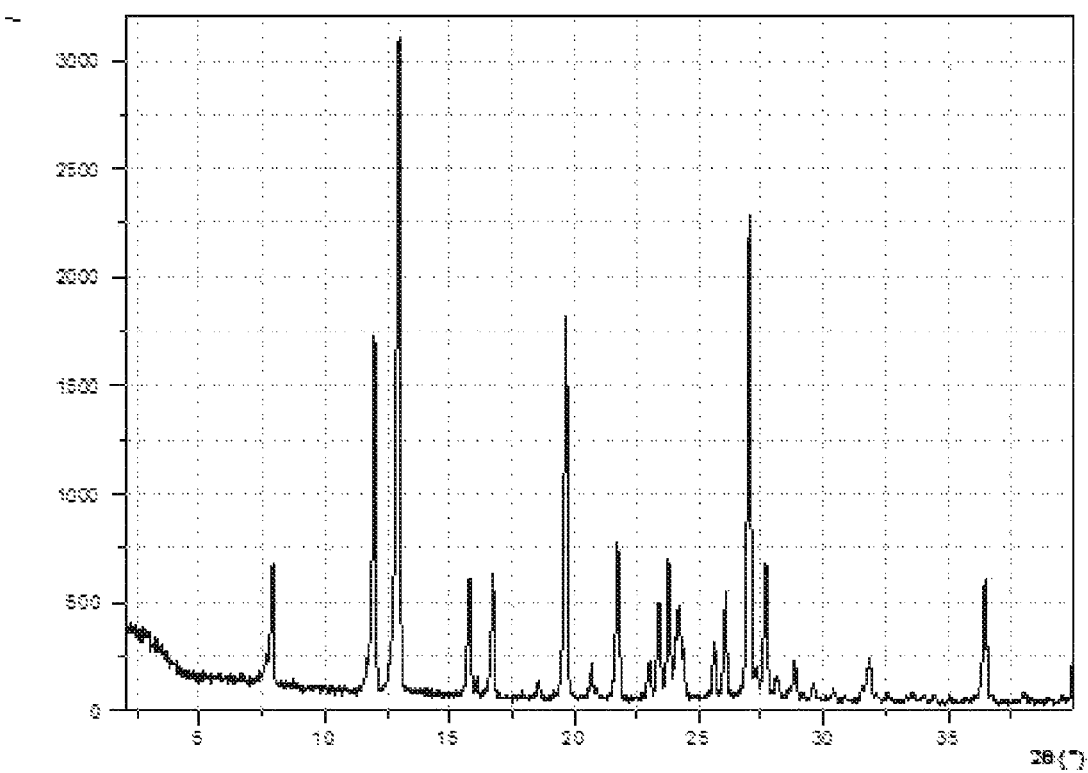
FIG. 1 is an X-ray powder diffractogram of a cocrystal of dimethyl fumarate and gentisic acid.

The present disclosure may be understood by reference to the following detailed description, taken in conjunction with the drawings as described above. It is noted that, for purposes of illustrative clarity, certain elements in various drawings may not be drawn to scale, may be represented schematically or conceptually, or otherwise may not correspond exactly to certain physical configurations of embodiments.

The term "Monomethyl fumarate" refers to the monomethyl ester of fumaric acid. The compound has the following chemical structure:

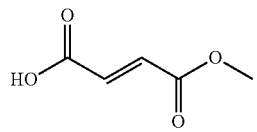

and has a molecular weight of 130.10 daltons. The compound is also commonly referred to as 2(E)-Butenedioic acid 1-methyl ester, (2E)-4-Methoxy-4-oxobut-2-enoic acid; Fumaric acid hydrogen 1-methyl ester; (2E)-2-Butenedioic acid 1-methyl ester; (E)-2-Butenedioic acid monomethyl ester; Monomethyl trans-ethylene-1,2-dicarboxylate; and methyl hydrogen fumarate. The compound is also referred to herein and elsewhere by the acronyms MMF and/or MHF.

The term "guest" as described herein refers to a compound other than dimethyl fumarate that is also a component of the cocrystal. Thus, the guest is part of the cocrystalline lattice. The guest is typically a GRAS (generally regarded as safe) compound and need not exhibit any therapeutic or pharmacological activity of its own. The Registry of Toxic Effects of Chemical Substances (RTECS) database is a useful source for toxicology information, and the GRAS list maintained by the RTECS contains about 2,500 relevant compounds that may be used in the generation of one or more cocrystals.

Cocrystals

Dimethyl fumarate is a prodrug of methyl hydrogen fumarate. Once administered, the compound is metabolized in vivo into an active metabolite, namely, methyl hydrogen fumarate (MHF) which is also referred to herein as monomethyl fumarate (MMF). The in vivo metabolism of dimethyl fumarate to MHF is illustrated below:

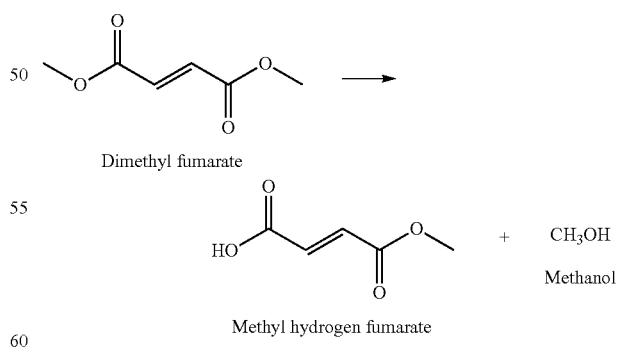

The present disclosure is directed to cocrystals of dimethyl fumarate.

By cocrystallizing the dimethyl fumarate with a guest, a new crystalline solid form is created having different properties from the dimethyl fumarate or the guest. For example, a cocrystal may have a different melting point, dissolution, solubility, hygroscopicity, bioavailability, toxicity, crystal morphology, density, loading volume, compressibility, physical stability, chemical stability, shelf life, taste, production costs, and/or manufacturing method than the crystalline prodrug.

Two different cocrystals of dimethyl fumarate are disclosed herein. The first is a cocrystal of dimethyl fumarate and gentisic acid. Other names for gentisic acid include 2,5-Dihydroxybenzoic acid (IUPAC); 2,5-Dihydroxybenzoic acid; 5-Hydroxysalicylic acid; Gentianic acid; Carboxyhydroquinone; 2,5-Dioxybenzoic acid; and Hydroquinonecarboxylic acid. Gentisic acid has the following chemical structure:

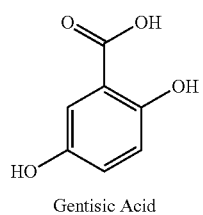

Gentisic Acid

Gentisic acid is a dihydroxybenzoic acid produced by carboxylation of hydroquinone. Gentisic acid is readily oxidized and is used as an antioxidant excipient in some pharmaceutical preparations.

The second is a cocrystal of dimethyl fumarate and (+)-camphoric acid. Other names for (+)-camphoric acid include (1R,3S)-1,2,2-trimethylcyclopentane-1,3-dicarboxylic acid (IUPAC); and acidum camphoricum. (+)-camphoric acid has the following chemical structure:

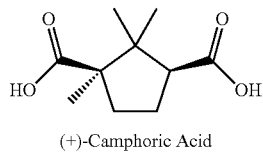

(+)-Camphoric Acid (+)-Camphoric acid is a white crystallisable substance obtained from the oxidation of camphor. It exists in three optically different forms; the dextrorotatory one is obtained by the oxidation of dextrorotatory camphor and is used in pharmaceuticals as a local antiseptic and to paralyze the nerve endings in sweat glands.

Two unique but structurally similar polymorph forms, cocrystal Form 1 and cocrystal Form 2, of dimethyl fumarate:(+)-camphoric acid cocrystal are isolated using methods described herein.

The melting points and water solubilities of dimethyl fumarate-gentisic acid cocrystal, crystalline dimethyl fumarate, and gentisic acid are shown in Table 1.

TABLE 1

Melting Point of DMF and Cocrystals of DMF and Gentisic Acid

| Crystal/Cocrystal | Crystal/ Cocrystal Melting Point (° C.) | Guest | Guest Melting Point (° C.) |
|---|---|---|---|
| dimethyl fumarate | 103 ± 1 | N/A | N/A |
| dimethyl fumarate: gentisic acid | 116 ± 2 | gentisic acid | 206 ± 2 |

As can be seen from the data in Table 1, the DMF-gentisic acid cocrystals exhibit a higher melting point than crystalline dimethyl fumarate.

Differential scanning calorimetry, or DSC, is a thermoanalytical technique in which the difference in the amount of heat required to increase the temperature of a sample and reference is measured as a function of temperature. DSC data shows differential heat flow plotted against temperature. As a sample undergoes a thermal event, it is effectively altering the heat flow due to the latent heat associated with the thermal event, which is then reflected as a peak or a shift in baseline. DSC can be used to characterize thermal properties of cocrystals, such as melting temperature or heat of fusion. Therefore, the melting point of the dimethyl fumarate cocrystals disclosed herein can be characterized by DSC.

In addition to melting point, there are other techniques that are commonly used to identify a cocrystal. For example, the chemical identity of the components of cocrystals can often be determined with solution-state techniques such as $^{13}C$ or $^{1}H$ NMR. However, while these solution-state techniques may help identify the prodrug and the guest, they do not provide any in formation about the cocrystalline solid-state structure. There are, however, several solid-state analytical techniques that can be used to provide information about solid-state structure including, for example, single crystal X-ray diffraction, powder X-ray diffraction, solid state $^{13}C$ NMR, Raman spectroscopy, and thermal techniques. Neither X-ray powder diffraction nor Raman spectroscopy themselves give direct data on the stoichiometry of the components which make up a cocrystal. There are techniques, however, that do provide such information. For example, single crystal X-ray diffraction gives a three-dimensional map of the atoms and bonds in the unit cell, thus directly providing the stoichiometry within the cocrystal and the precise stoichiometry within the unit cell. Solution-state techniques such as NMR may be used to confirm the molar ratios of the cocrystal component species.

Single-crystal X-ray diffraction provides three-dimensional structural information about the positions of atoms and bonds in a cocrystal. It is not always possible or feasible, however, to obtain such a structure from a cocrystal due to, for example, insufficient crystal size or difficulty in preparing crystals of sufficient quality for single-crystal X-ray diffraction. Structural identification information can, however, be obtained from other solid-state techniques such as X-ray powder diffraction and Raman spectroscopy. These techniques are used to generate data on a solid cocrystal. Once that data has been collected on a known cocrystal, that data can be used to identify the presence of that cocrystal in other materials. Thus, these data effectively characterize the cocrystal. For example, an X-ray powder diffraction pattern, or a portion thereof, can serve as a fingerprint which characterizes a cocrystal and differentiates the cocrystal from its component parts (i.e., prodrug and guest) thereby showing that the cocrystal is indeed a new material and not simply a physical mixture of the prodrug and the guest.

An X-ray powder diffraction plot is an x-y graph with scattering angles 2θ (diffraction) on the x-axis and intensity on the y-axis. The peaks within this plot can be used to characterize a cocrystal. Although the peaks within an entire diffractogram can be used to characterize a cocrystal, a subset of the more characteristic peaks can also be used to accurately characterize a cocrystal. The data is often represented by the position of the peaks on the x-axis rather than the intensity of peaks on the y-axis because peak intensity may vary with sample orientation. There is also variability in the position of peaks on the x-axis. There are several sources of this variability, one of which comes from sample preparation. Samples of the same cocrystalline material prepared under different conditions may yield slightly different diffractograms. Factors such as particle size, moisture content, solvent content, and orientation can affect how a sample diffracts X-rays. Another source of variability comes from instrument parameters. Different X-ray instruments operate using different parameters and these may lead to slightly different diffraction patterns from the same cocrystal. Likewise, different software packages process X-ray data differently and this also leads to variability. These and other sources of variability are known to those of ordinary skill in the pharmaceutical arts. Due to these sources of variability, it is common to recite X-ray diffraction peaks using the word "about" prior to the peak value in 2θ. The word "about" incorporates this variability which under most sampling conditions, and most data collection and data processing conditions, leads to a variability in peak position of about plus or minus 0.2 scattering angle (2θ). Thus, when a peak is said to be at about 10.5 scattering angle (2θ), under most sampling, data collection, and data processing conditions, that peak will appear anywhere between 10.3 (2θ) and 10.7 (2θ). In characterizing the cocrystals disclosed herein, the X-ray diffraction peaks were all measured using Cu—K$_\alpha$ radiation and all peaks herein cited refer to peaks diffracted from X-rays with that wavelength.

Dimethyl Fumarate:Gentisic Acid Cocrystal

One cocrystal disclosed herein is a cocrystal of dimethyl fumarate and gentisic acid. The cocrystal is prepared from a suspension of DMF and gentisic acid in a mixture of ethyl acetate and heptane. In certain embodiment, the stoichiometry of dimethyl fumarate to gentisic acid is about 1:3 to about 1:1. In certain embodiment, the stoichiometry of dimethyl fumarate to gentisic acid is about 1:25 to about 1:15. In a particular embodiment, the stoichiometry of dimethyl fumarate to gentisic acid is about 1:2. Differential scanning calorimetry (DSC) analysis of this cocrystal shows a melting point between about 114° C. and about 118° C., in certain embodiments between about 115° C. and about 117° C., and in certain embodiments at about 116° C.

FIG. 1 is an X-ray powder diffractogram showing the diffraction pattern measured using Cu—K$_\alpha$ radiation of the dimethyl fumarate:gentisic acid cocrystal. Tables 2 and 3 lists the approximate numerical values of the XRPD peak positions of the FIG. 1 diffractogram. While the entire diffractogram of FIG. 1 can be used to characterize the cocrystal, the cocrystal can also be accurately characterized with a subset of that data. For example, the peaks within Table 2, listed in order of their peak height/intensity, are the more unique and thus more characteristic of the dimethyl fumarate:gentisic acid cocrystal.

TABLE 2

Characteristic XRPD Peaks for dimethyl fumarate: gentisic acid cocrystal

| Peak Position (°2θ) | Peak Height (counts) | Peak Relative Intensity (%) |
| --- | --- | --- |
| 13.0 | 2784 | 100 |
| 12.0 | 1544 | 55.5 |
| 21.8 | 650 | 23.4 |
| 23.8 | 641 | 23.0 |
| 27.7 | 626 | 22.5 |
| 16.8 | 563 | 20.2 |
| 36.5 | 548 | 19.7 |
| 8.0 | 522 | 18.8 |
| 26.1 | 472 | 17.0 |
| 15.9 | 451 | 16.2 |
| 23.4 | 436 | 15.7 |
| 24.4 | 204 | 7.3 |
| 23.0 | 173 | 6.2 |
| 31.9 | 164 | 5.9 |
| 20.7 | 137 | 4.9 |
| 29.6 | 67 | 2.4 |

The additional dimethyl fumarate:gentisic acid cocrystal XRPD peaks that may have less characteristic relevance, are listed in Table 3.

TABLE 3

Additional XRPD Peaks for dimethyl fumarate: gentisic acid cocrystal

| Peak Position (°2θ) | Peak Height (counts) | Peak Relative Intensity (%) |
| --- | --- | --- |
| 27.0 | 2183 | 78.4 |
| 19.7 | 1701 | 61.1 |
| 24.2 | 407 | 14.6 |
| 25.6 | 241 | 8.7 |
| 28.8 | 181 | 6.5 |
| 27.3 | 151 | 5.4 |
| 28.1 | 98 | 3.5 |
| 18.6 | 68 | 2.5 |
| 16.1 | 63 | 2.3 |
| 38.0 | 48 | 1.7 |
| 32.6 | 37 | 1.3 |
| 34.4 | 30 | 1.1 |
| 30.4 | 28 | 1.0 |
| 33.4 | 19 | 0.7 |
| 35.1 | 16 | 0.6 |

In certain embodiments, the dimethyl fumarate:gentisic acid cocrystal exhibits a characteristic scattering angle (2θ) at least at 13.0±0.2° in an X-ray powder diffraction pattern measured using Cu—K$_\alpha$ radiation.

In certain embodiments, the dimethyl fumarate:gentisic acid cocrystal exhibits characteristic scattering angles (2θ) at least at 13.0±0.2°, 12.0±0.2°, 21.8±0.2°, 23.8±0.2°, and 27.7±0.2° in an X-ray powder diffraction pattern measured using Cu—K$_\alpha$ radiation.

In certain embodiments, the dimethyl fumarate:gentisic acid cocrystal exhibits characteristic scattering angles (2θ) at least at 13.0±0.2°, 12.0±0.2°, 21.8±0.2°, 23.8±0.2°, 27.7±0.2°, 16.8±0.2°, 36.5±0.2°, 8.0±0.2°, 26.1±0.2° and 15.9±0.2° in an X-ray powder diffraction pattern measured using Cu—K$_\alpha$ radiation.

In certain embodiments, the dimethyl fumarate:gentisic acid cocrystal exhibits characteristic scattering angles (2θ) at least at 13.0±0.2°, 12.0±0.2°, 21.8±0.2°, 23.8±0.2°, 27.7±0.2°, 16.8±0.2°, 36.5±0.2°, 8.0±0.2°, 26.1±0.2°, 15.9±0.2°, 23.4±0.2°, 24.4±0.2°, 23.0±0.2°, 31.9±0.2°, 20.7±0.2°, and 29.6±0.2° in an X-ray powder diffraction pattern measured using Cu—K$_\alpha$ radiation.

Figure 2:
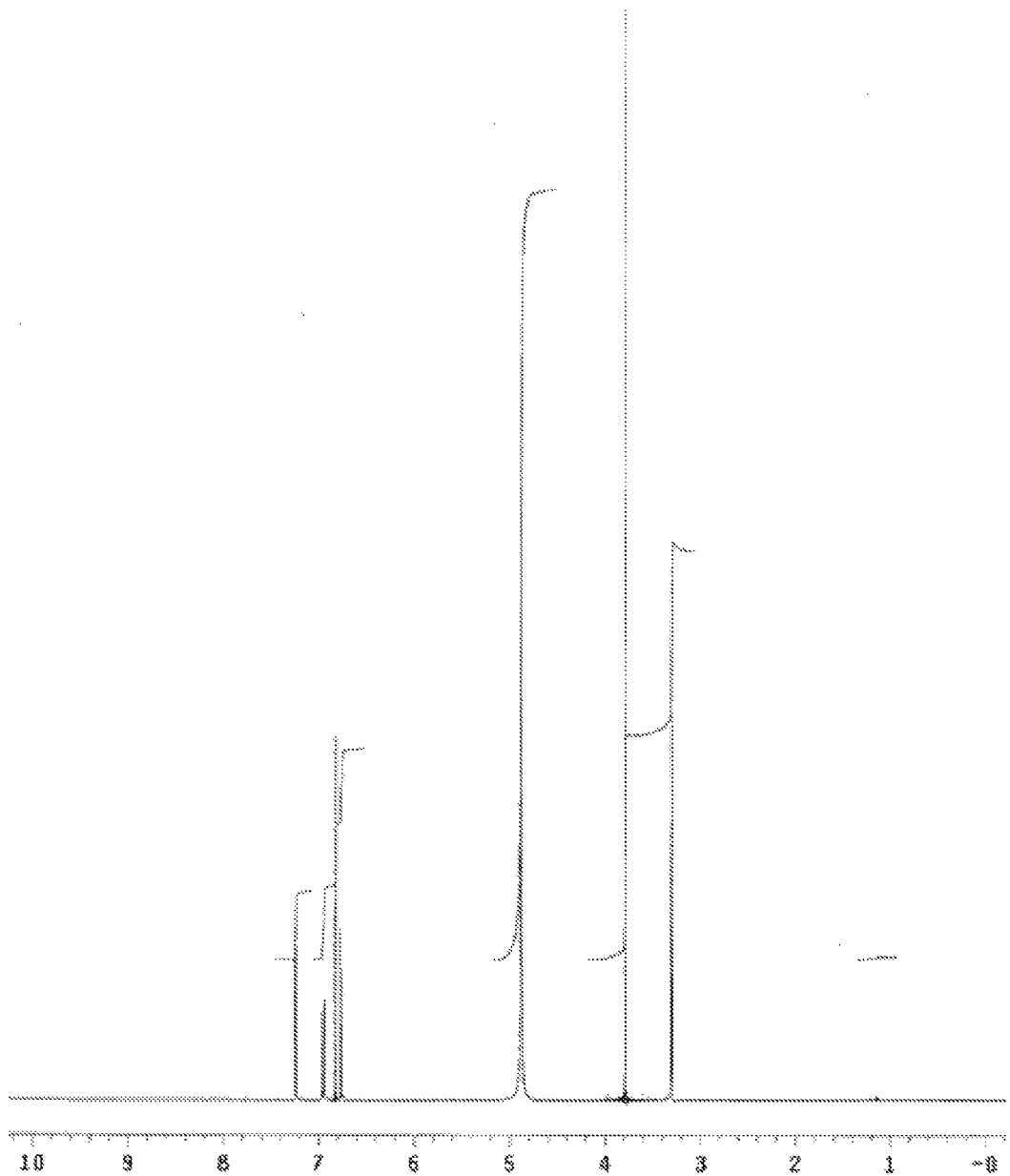
FIG. 2 is a spectrogram showing the nuclear magnetic resonance (NMR) spectral pattern of a cocrystal of dimethyl fumarate and gentisic acid.

FIG. 2 is a spectrogram showing the NMR spectrum of the dimethyl fumarate:gentisic acid cocrystal. The NMR spectral pattern indicates $^1$H NMR (MeOH-d$_3$, 400 MHz): δ 7.22 (s, 1H), 6.95 (d, 1H), 6.80 (s, 2H), 6.76 (d, 1H), 179 (s, 3H) for the dimethyl fumarate:gentisic acid cocrystal. NMR data shows that the stoichiometry of dimethyl fumarate to gentisic acid is about 1:2.

Figure 3:
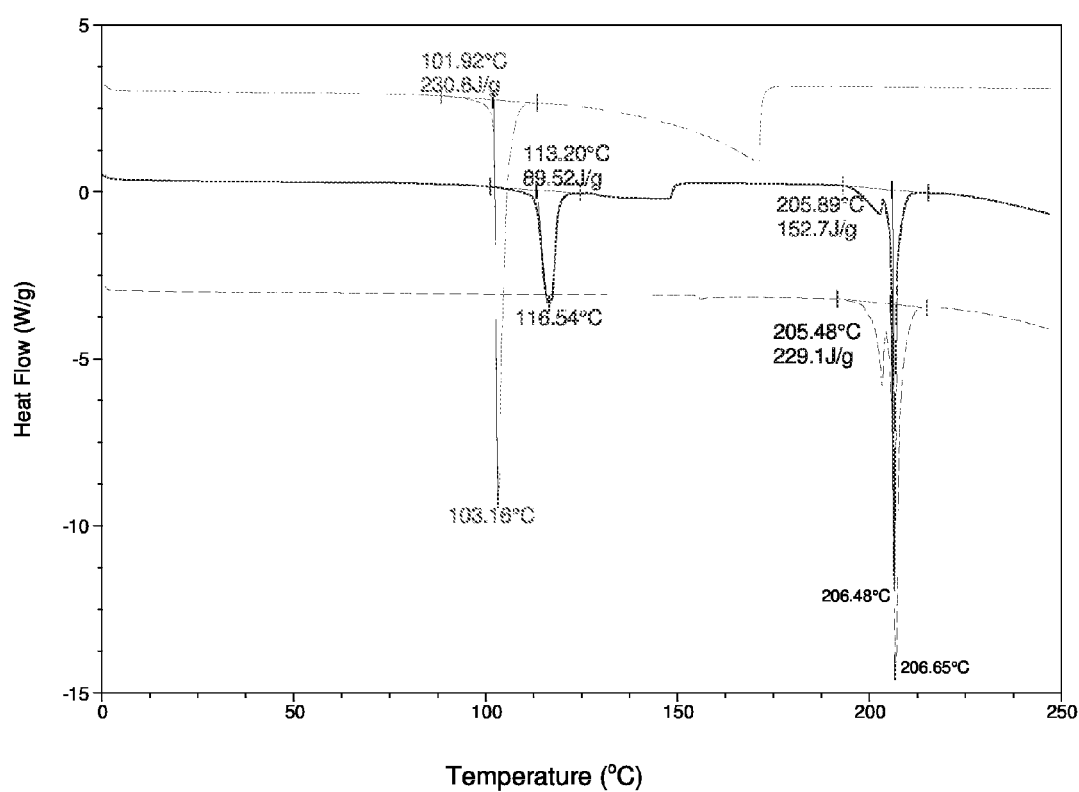
FIG. 3 is a differential scanning calorimetry (DSC) thermogram of dimethyl fumarate (upper), a cocrystal of dimethyl fumarate and gentisic acid (middle), and gentisic acid (lower).

FIG. 3 is a DSC thermogram of the dimethyl fumarate:gentisic acid cocrystal. The thermogram shows the cocrystal has a melting point of about 114 to 118° C.

The dimethyl fumarate:gentisic acid cocrystal is expected to have a good toxicology profile. Furthermore, under physiological conditions, the cocrystal is expected to enhance super-saturation of dissolved dimethyl fumarate, and thus would have improved absorption and bioavailability over crystalline dimethyl fumarate.

Dimethyl Fumarate:(+)-Camphoric Acid Cocrystal Form 1

Another cocrystal disclosed herein is a cocrystal of dimethyl fumarate and (+)-camphoric acid. The cocrystal is isolated by adding heptane to a solution of DMF and (+)-camphoric acid in ethyl acetate.

In one embodiment, the solution cocrystallization forms large well formed clear rods of cocrystal. In one embodiment, the cocrystal is solvated with solvents of the crystallization. In one embodiment, the ratios of the components of the solvated cocrystal depend on the condition of the solution crystallization. In one embodiment, the cocrystal comprises DMF, (+)-camphoric acid, ethyl acetate and heptanes.

Figure 4:
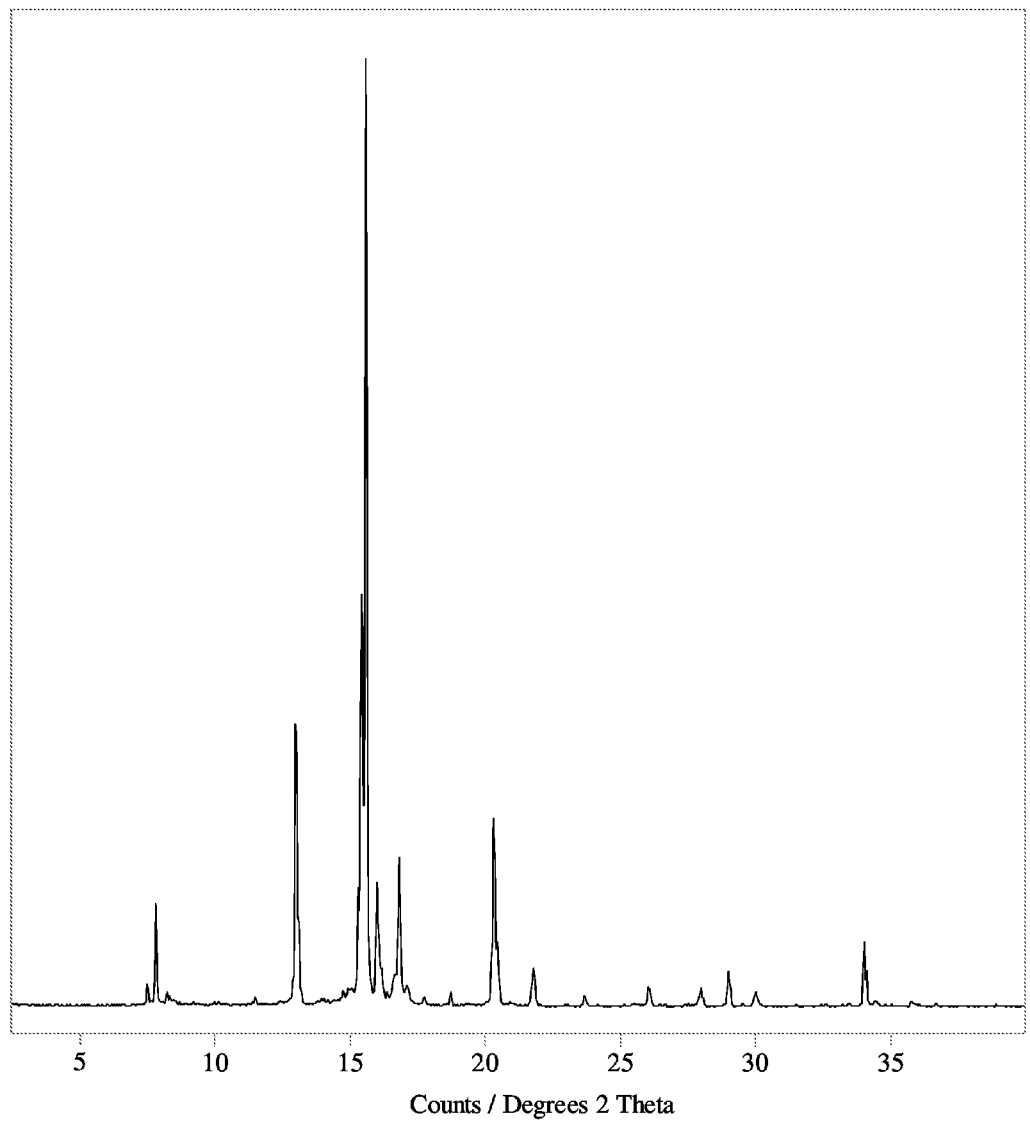
FIG. 4 is an X-ray powder diffractogram of a cocrystal of dimethyl fumarate and (+)-camphoric acid form 1, isolated from solution.

FIG. 4 is an X-ray powder diffractogram showing the diffraction pattern measured using Cu—K$_\alpha$ radiation of the dimethyl fumarate:(+)-camphoric acid cocrystal form 1. Table 4 lists the approximate numerical values of the XRPD peak positions of the FIG. 4 diffractogram. While the entire diffractogram of FIG. 4 can be used to characterize the cocrystal, the cocrystal can also be accurately characterized with a subset of that data. For example, the XRPD peak at 15.6° 2θ characterizes the dimethyl fumarate:(+)-camphoric acid cocrystal form 1.

TABLE 4

Characteristic XRPD Peaks for dimethyl fumarate: (+)-camphoric acid cocrystal form 1

| Peak Position (°2θ) | Peak Height (counts) | Peak Relative Intensity (%) |
|---|---|---|
| 15.6 | 17490 | 100 |
| 15.4 | 7622 | 43.6 |
| 20.3 | 3507 | 20.1 |
| 16.0 | 2319 | 13.3 |
| 7.8 | 1913 | 10.9 |
| 8.2 | 300 | 1.7 |
| 18.7 | 298 | 1.7 |

The additional dimethyl fumarate:(+)-camphoric acid cocrystal form 1 XRPD peaks that may have less characteristic relevance, are listed in Table 5.

TABLE 5

Additional XRPD Peaks for dimethyl fumarate: (+)-camphoric acid Cocrystal Form 1

| Peak Position (°2θ) | Peak Height (counts) | Peak Relative Intensity (%) |
|---|---|---|
| 13.0 | 5246 | 30.0 |
| 16.8 | 2772 | 15.8 |
| 26.0 | 396 | 2.3 |
| 21.8 | 735 | 4.2 |
| 23.7 | 221 | 1.3 |
| 7.5 | 440 | 2.5 |
| 17.7 | 213 | 1.2 |
| 30.0 | 295 | 1.7 |

The XRPD peak at 15.4° 2θ is another peak that alone or together with the peak at 15.6° 2θ characterizes the dimethyl fumarate:(+)-camphoric acid cocrystal form 1.

Likewise, the peak at 20.3° 2θ is another peak that alone or together with the peaks at 15.6 and/or 15.4° 2θ characterizes the dimethyl fumarate:(+)-camphoric acid cocrystal form 1.

Also, the peak at 16.0° 2θ is another peak that alone or together with the peaks at 15.6° 2θ. 15.4° 2θ, and/or 20.3° 2θ characterizes the dimethyl fumarate:(+)-camphoric acid cocrystal form 1.

In certain embodiments, the dimethyl fumarate:(+)-camphoric acid cocrystal form 1 exhibits characteristic scattering angles (2θ) at least at 15.6±0.2°, 15.4±0.2°, 20.3±0.2°, 16.0±0.2°, and 7.8±0.2° in an X-ray powder diffraction pattern measured using Cu—K$_\alpha$ radiation.

In certain embodiments, the dimethyl fumarate:(+)-camphoric acid cocrystal form 1 exhibits characteristic scattering angles (2θ) at least at 15.6±0.2°, 15.4±0.2°, 20.3±0.2°, 16.0±0.2°, 7.8±0.2°, 8.2±0.2°, and 18.7±0.2° in an X-ray powder diffraction pattern measured using Cu—K$_\alpha$ radiation.

Figure 5:
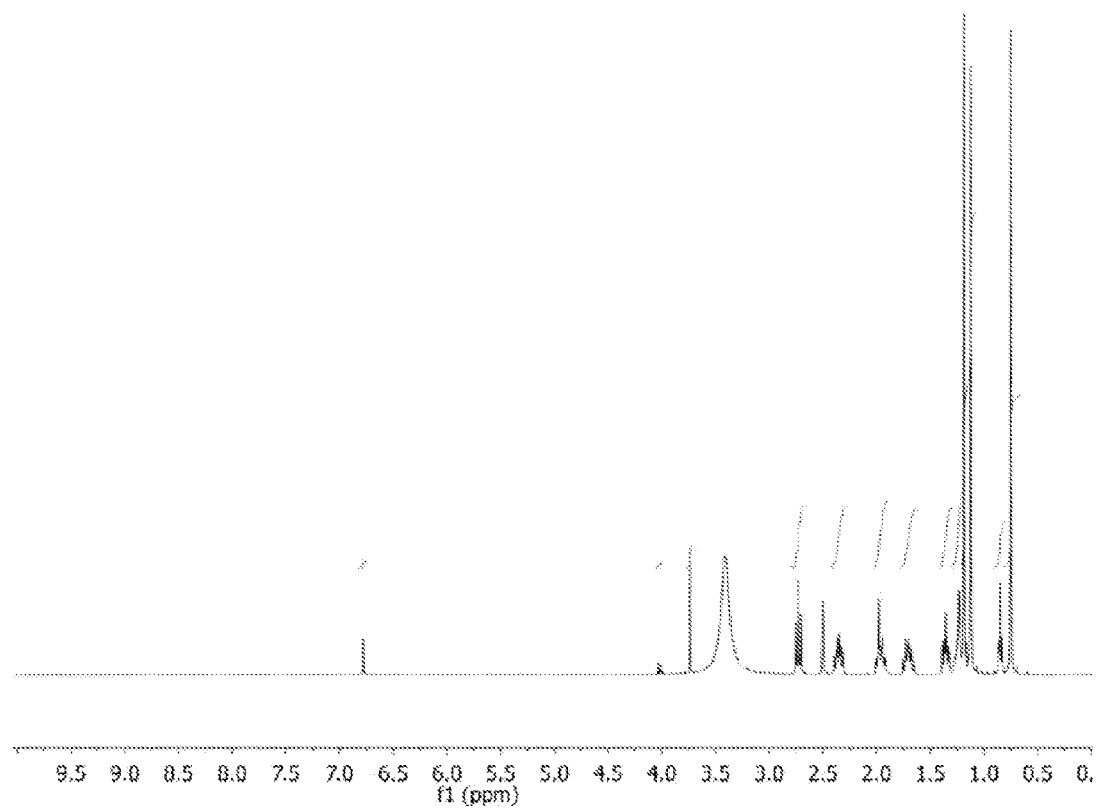
FIG. 5 is a spectrogram showing the NMR spectral pattern of a cocrystal of dimethyl fumarate and (+)-camphoric acid form 1, isolated from solution.

FIG. 5 is a spectrogram showing the NMR spectrum of the dimethyl fumarate:(+)-camphoric acid cocrystal form 1. The NMR spectral pattern indicates $^1$H NMR (DMSO-d$_6$, 400 MHz): δ 6.78 (s, 0.09H), 3.73 (s, 0.37H), 2.72 (t, 1.04H), 2.35 (m, 1.01H), 1.95 (m, 0.98H), 1.68 (m, 0.98H), 1.35 (m, 1H), 1.18 (s, 3.02H), 1.111 (s, 3.02H), 0.73 (s, 2.89H) for the dimethyl fumarate:(+)-camphoric acid cocrystal form 1.

Figure 6:
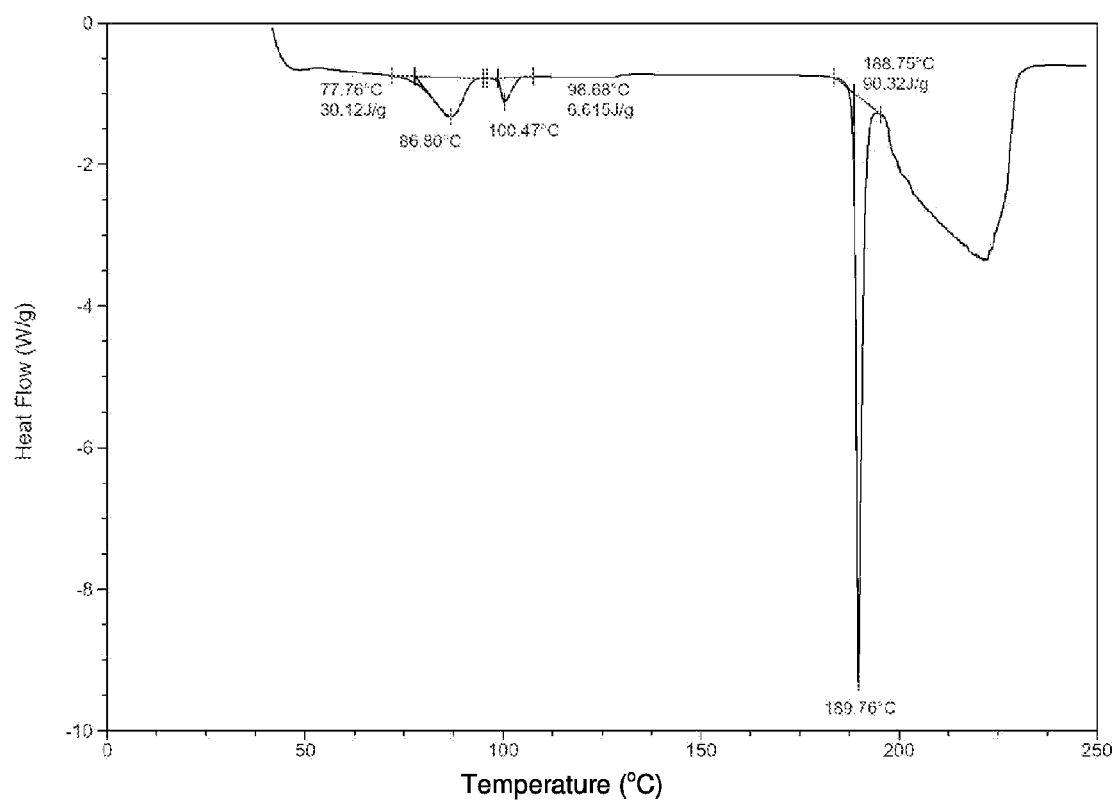
FIG. 6 is a differential scanning calorimetry (DSC) thermogram, measured using a crimped pan, of a cocrystal of dimethyl fumarate and (+)-camphoric acid form 1, isolated from solution.
Figure 7:
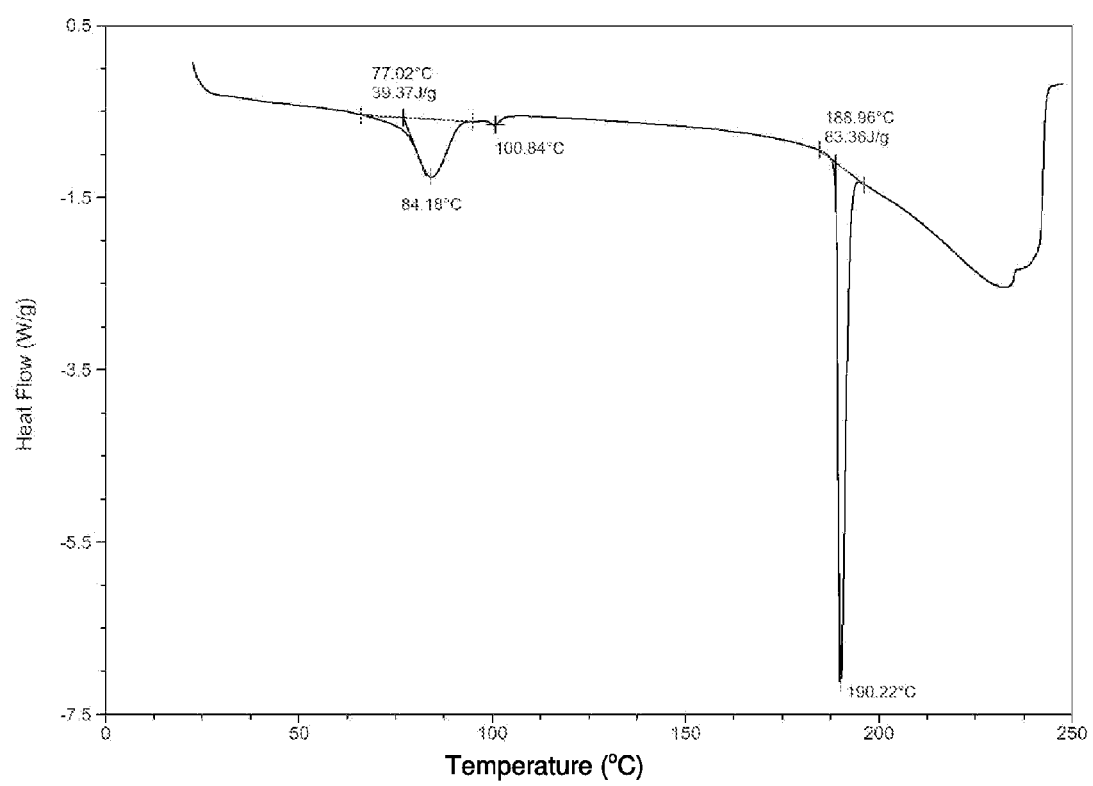
FIG. 7 is a differential scanning calorimetry (DSC) thermogram, measured using an open pan, of a cocrystal of dimethyl fumarate and (+)-camphoric acid form 1, isolated from solution.

FIG. 6 is a DSC thermogram of the dimethyl fumarate:(+)-camphoric acid cocrystal form 1 using a crimped pan whereas FIG. 7 is a DSC thermogram of the dimethyl fumarate:(+)-camphoric acid cocrystal form 1 using an open pan. The thermograms show the cocrystal has melting point between about 77° C. and about 94° C.; when measured in a crimped pan; and the cocrystal has melting point between about 77° C. and about 98° C.; when measured in a open pan.

In certain embodiments, the differential scanning calorimetry (DSC) analysis of this cocrystal in crimped pan shows a melting point between about 80° C. and about 92° C., in certain embodiments between about 83° C. and about 90° C., and in certain embodiments at about 87° C.

In certain embodiments, the differential scanning calorimetry (DSC) analysis of this cocrystal in open pan shows a melting point between about 79° C. and about 95° C., in certain embodiments between about 80° C. and about 90° C., and in certain embodiments at about 84° C.

The dimethyl fumarate:(+)-camphoric acid cocrystal form 1 is expected to have a good toxicology profile.

Dimethyl Fumarate:(+)-Camphoric Acid Cocrystal Form 2

Another cocrystal disclosed herein is a cocrystal of dimethyl fumarate and (+)-camphoric acid. The cocrystal is isolated by grinding a mixture of DMF and (+)-camphoric acid in a ball mill in the presence of a drop of solvent. NMR data indicates that the stoichiometry of dimethyl fumarate to (+)-camphoric acid is about 1:4.

Figure 8:
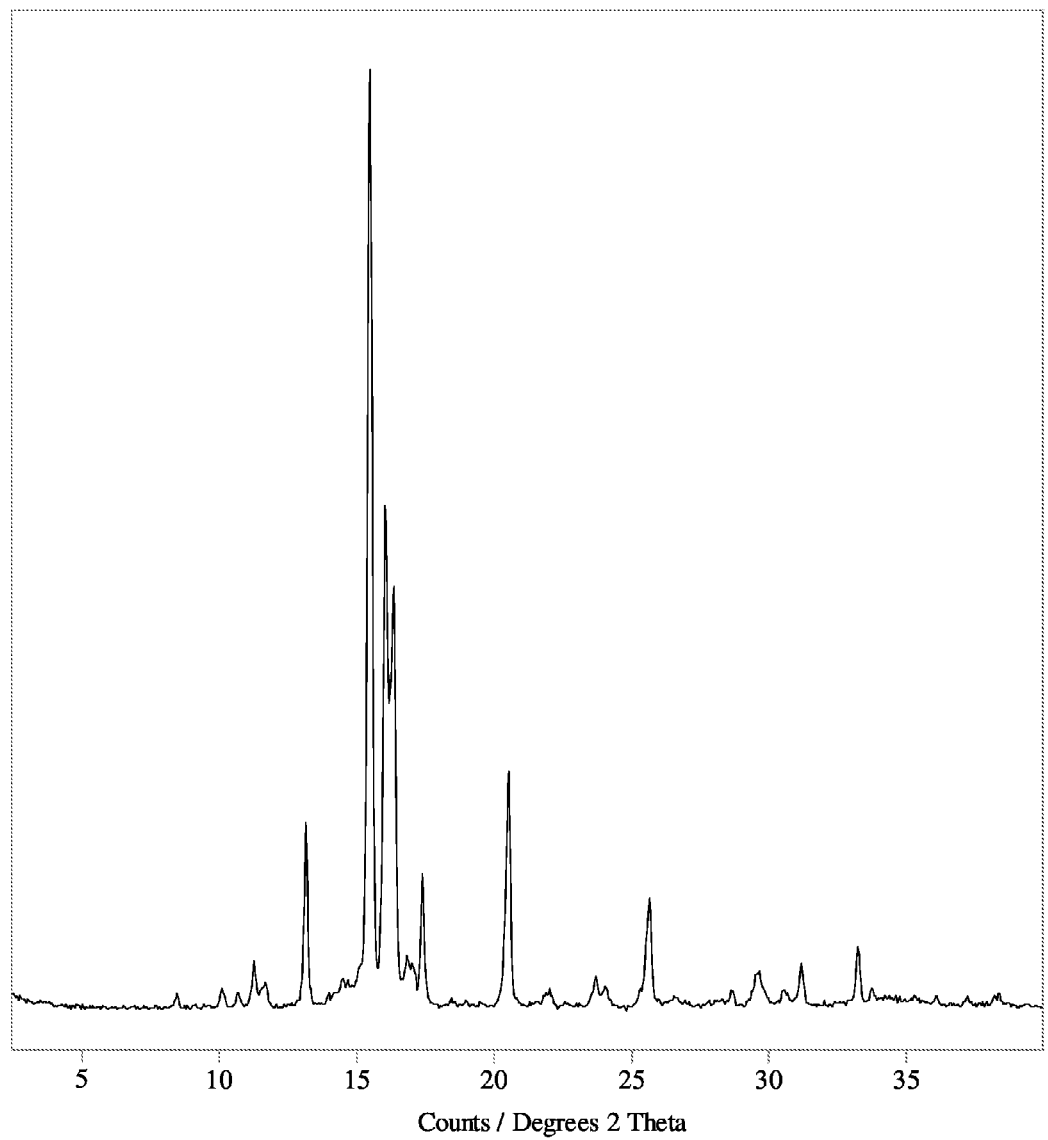
FIG. 8 is an X-ray powder diffractogram of a cocrystal of dimethyl fumarate and (+)-camphoric acid form 2, isolated from milling.

FIG. 8 is an X-ray powder diffractogram showing the diffraction pattern measured using Cu—K$_\alpha$ radiation of the dimethyl fumarate:(+)-camphoric acid cocrystal form 2. Table 6 lists the approximate numerical values of the XRPD peak positions of the FIG. 8 diffractogram.

TABLE 6

Characteristic XRPD Peaks for dimethyl fumarate: (+)-camphoric acid cocrystal form 2

| Peak Position (°2θ) | Peak Height (counts) | Peak Relative Intensity (%) |
|---|---|---|
| 15.5 | 4788 | 100 |
| 16.1 | 2577 | 53.8 |
| 20.5 | 1232 | 25.7 |

TABLE 6-continued

Characteristic XRPD Peaks for dimethyl fumarate: (+)-camphoric acid cocrystal form 2

| Peak Position (°2θ) | Peak Height (counts) | Peak Relative Intensity (%) |
|---|---|---|
| 31.2 | 256 | 5.3 |
| 29.6 | 216 | 4.5 |
| 10.1 | 130 | 2.7 |

The additional dimethyl fumarate:(+)-camphoric acid cocrystal form 2 XRPD peaks that may have less characteristic relevance, are listed in Table 7.

TABLE 7

Additional XRPD Peaks for dimethyl fumarate: (+)-camphoric acid Cocrystal Form 2

| Peak Position (°2θ) | Peak Height (counts) | Peak Relative Intensity (%) |
|---|---|---|
| 13.2 | 972 | 20.3 |
| 25.6 | 591 | 12.3 |
| 16.3 | 2172 | 45.4 |
| 17.0 | 257 | 5.4 |
| 11.3 | 274 | 5.7 |
| 11.7 | 161 | 3.4 |
| 10.7 | 109 | 2.3 |
| 23.7 | 193 | 4.0 |
| 24.1 | 144 | 3.0 |
| 33.3 | 345 | 7.2 |

While the entire diffractogram of FIG. 8 can be used to characterize the cocrystal, the cocrystal can also be accurately characterized with a subset of that data. For example, the peak at about 15.5° 2θ characterizes the dimethyl fumarate:(+)-camphoric acid cocrystal form 2.

The XRPD peak at about 16.1° 2θ is another peak that alone or together with the peak at 15.5° 2θ characterizes the dimethyl fumarate:(+)-camphoric acid cocrystal form 2.

Likewise, XRPD peak at about 20.5° 2θ is another peak that alone or together with the peaks at 15.5 and/or 16.1° 2θ characterizes the dimethyl fumarate:(+)-camphoric acid cocrystal form 2.

Also, XRPD peaks at 15.5° 2θ. 16.1° 2θ, and/or 20.5° 2θ characterizes the dimethyl fumarate:(+)-camphoric acid cocrystal form 2.

In certain embodiments, the dimethyl fumarate:(+)-camphoric acid cocrystal form 2 exhibits characteristic scattering angles (2θ) at least at 15.5±0.2°, 16.1±0.2°, 20.5±0.2°, 31.2±0.2°, and 29.6±0.2° in an X-ray powder diffraction pattern measured using Cu—K$_\alpha$ radiation.

In certain embodiments, the dimethyl fumarate:(+)-camphoric acid cocrystal form 2 exhibits characteristic scattering angles (2θ) at least at 15.5±0.2°, 16.1±0.2°, 20.5±0.2°, 31.2±0.2°, 29.6±0.2° and 10.1±0.2° in an X-ray powder diffraction pattern measured using Cu—K$_\alpha$ radiation.

Figure 9:
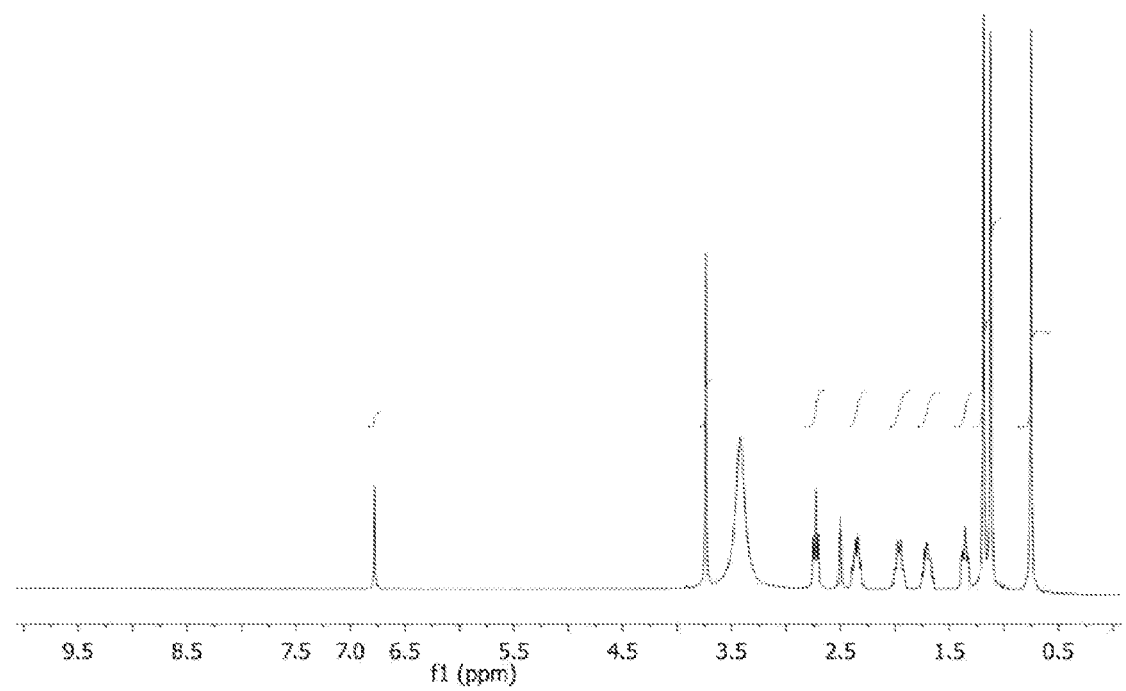
FIG. 9 is a spectrogram showing the NMR spectral pattern of a cocrystal of dimethyl fumarate and (+)-camphoric acid form 2, isolated from milling.

FIG. 9 is a spectrogram showing the NMR spectrum of the dimethyl fumarate:(+)-camphoric acid cocrystal form 2. The NMR spectral pattern indicates $^1$H NMR (DMSO-d$_6$, 400 MHz): δ 6.76 (s, 1H), 3.75 (s, 6H), 2.72 (t, 1H), 2.38 (m, 1H), 1.96 (m, 1H), 1.63 (m, 1H), 1.37 (m, 1H), 1.18 (s, 3.02H), 1.09 (s, 3H), 0.74 (s, 3H) for the dimethyl fumarate:(+)-camphoric acid cocrystal form 2.

Figure 10:
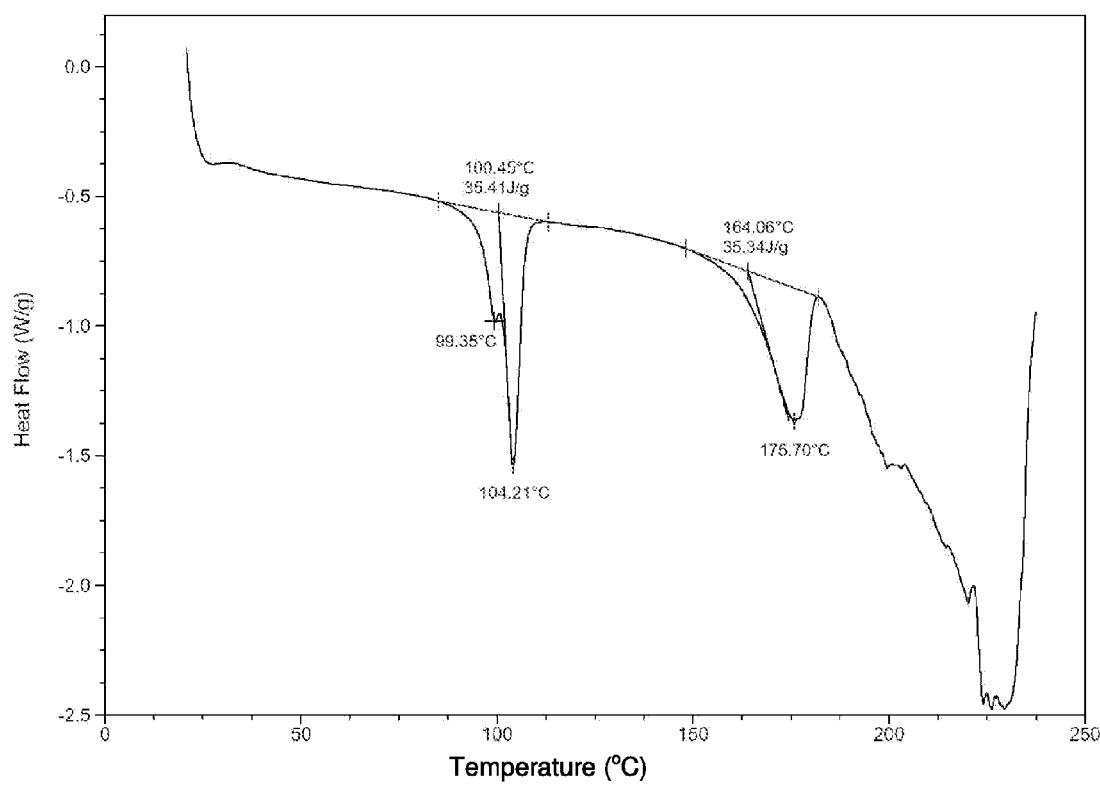
FIG. 10 is a differential scanning calorimetry (DSC) thermogram, measured using a crimped pan, of a cocrystal of dimethyl fumarate and (+)-camphoric acid form 2, isolated from milling.
Figure 11:
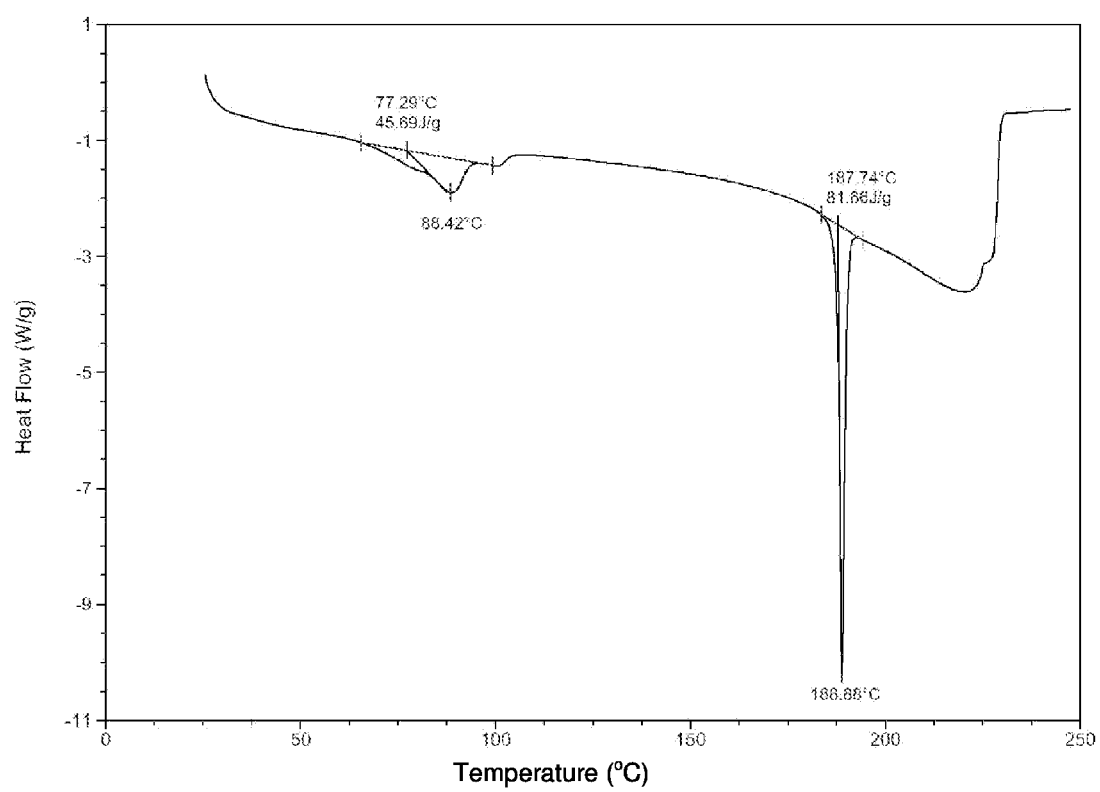
FIG. 11 is a differential scanning calorimetry (DSC) thermogram, measured using an open pan, of a cocrystal of dimethyl fumarate and (+)-camphoric acid form 2, isolated from milling.

FIG. 10 is a DSC thermogram of the dimethyl fumarate:(+)-camphoric acid cocrystal form 2 using a crimped pan whereas FIG. 11 is a DSC thermogram of the dimethyl fumarate:(+)-camphoric acid cocrystal form 2 using an open pan. The thermograms show the cocrystal has melting point between about 80° C. and about 96° C.; when measured in a open pan. In certain embodiments, the cocrystal has melting point between about 84° C. and about 92° C. In certain embodiments, the cocrystal has melting point between about 86° C. and about 90° C.

The dimethyl fumarate:(+)-camphoric acid cocrystal form 2 is expected to have a good toxicology profile.

Pharmaceutical Compositions

The present disclosure relates to pharmaceutical compositions comprising a therapeutically effective amount of a cocrystal disclosed herein and a pharmaceutically acceptable carrier (also known as a pharmaceutically acceptable excipient). The cocrystals disclosed herein have the same pharmaceutical activity as their respective active pharmaceutical ingredient (API). Pharmaceutical compositions for the treatment of any one or more diseases and disorders contain a therapeutically effective amount of a cocrystal disclosed herein as appropriate for treatment of a patient with the particular disease(s) or disorder(s).

A "therapeutically effective amount" of a disclosed cocrystal (discussed here concerning the pharmaceutical compositions) refers to an amount sufficient to produce the desired therapeutic effect, for example, an amount that is sufficient to reduce inflammation, an amount that is sufficient to achieve a desired autoimmune response, or an amount sufficient to prevent, kill, or inhibit the growth of tumor cells. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; the rate of excretion of a disclosed cocrystal; the duration of the treatment; any drugs used in combination or coincidental with the specific compound employed; the discretion of the prescribing physician; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001.

A pharmaceutical composition may be any pharmaceutical form which maintains the crystalline form of a disclosed cocrystal. In certain embodiments, the pharmaceutical composition may be selected from a solid form such as a solid oral dosage form, a liquid suspension, an injectable composition, a topical form, and a transdermal form.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition comprising a cocrystal disclosed herein, a carrier should be chosen that maintains the cocrystal. In other words, the carrier should not substantially alter the crystalline form of the cocrystal. For example, a liquid carrier which would dissolve the cocrystal would not be indicated for uses in which it is desired to maintain the cocrystalline forms disclosed herein. Nor should the carrier be otherwise incompatible with a cocrystal, such as by producing any undesirable biological effect or otherwise interacting in a deleterious manner with any other component(s) of the pharmaceutical composition.

In some embodiments, the pharmaceutical compositions are formulated in unit dosage forms for ease of administration and uniformity of dosage. A "unit dosage form" refers to a physically discrete unit of therapeutic agent appropriate for the patient to be treated. It will be understood, however, that the total daily dosage of a cocrystal and its pharmaceutical compositions will typically be decided by the attending physician within the scope of sound medical judgment.

Because the crystalline form of a cocrystal disclosed herein is more easily maintained during their preparation, solid dosage forms may be employed in numerous embodiments for the pharmaceutical compositions. In some embodiments, solid dosage forms for oral administration include capsules, tablets, pills, powders, and granules. In such solid dosage forms, the active compound is mixed with at least one pharmaceutically acceptable carrier, such as for example sodium citrate or dicalcium phosphate. The solid dosage form may also include one or more of: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate. The solid dosage forms may also comprise buffering agents. They may optionally contain opacifying agents and can also be of a composition such that they release the active ingredient(s) only in a certain part of the intestinal tract, optionally, in a delayed manner. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions can also be prepared with coatings and shells such as enteric coatings and other coatings well known in the pharmaceutical formulating art.

A cocrystal disclosed herein can be in a solid microencapsulated form with one or more carriers as discussed above. Microencapsulated forms of a cocrystal may also be used in soft and hard-filled gelatin capsules with carriers such as lactose or milk sugar as well as high molecular weight polyethylene glycols and the like.

Also disclosed herein are methods for the treatment of the disorders disclosed herein. The cocrystals, and pharmaceutical compositions comprising them, may be administered using any amount, any form of pharmaceutical composition and any route of administration effective for the treatment. After formulation with an appropriate pharmaceutically acceptable carrier in a desired dosage, as known by those of skill in the art, the pharmaceutical compositions can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In certain embodiments, the cocrystals may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject.

Therapeutic Uses

The dimethyl fumarate cocrystals disclosed herein may be used to treat diseases, disorders, conditions, and/or symptoms of any disease or disorder for which DMF and/or MMF is known to provide, or is later found to provide, therapeutic benefit. DMF and MMF are known to be effective in treating psoriasis, multiple sclerosis, an inflammatory bowel disease, asthma, chronic obstructive pulmonary disease, and arthritis. Hence, the dimethyl fumarate cocrystals disclosed herein may be used to treat any one or more of the foregoing diseases and disorders. The underlying etiology of any of the foregoing diseases being treated may have a multiplicity of origins. Further, in certain embodiments, a therapeutically effective amount of one or more of the dimethyl fumarate cocrystals may be administered to a patient, such as a human, as a preventative measure against various diseases or disorders. Thus, a therapeutically effective amount of one or more of the dimethyl fumarate cocrystals may be administered as a preventative measure to a patient having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases (such as Parkinson's disease, Alzheimer's disease, Huntington's disease, retinopathia pigmentosa and mitochondrial encephalomyopathy), transplantation rejection, autoimmune diseases including multiple sclerosis, ischemia and reperfusion injury, AGE-induced genome damage, inflammatory bowel diseases such as Crohn's disease and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, *Trends Mol Med* (2005), 11(1): 43-48; and Mrowietz et al., *Br J Dermatology* (1999), 141: 424-429).

Efficacy of the dimethyl fumarate cocrystals for treating psoriasis can be determined using animal models and in clinical trials.

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis, among others. The pathogenesis of immune-mediated inflammatory diseases including inflammatory arthritis is believed to involve TNF and NK-κB signaling pathways (Tracey et al., *Pharmacology & Therapeutics* (2008), 117: 244-279). Dimethyl fumarate has been shown to inhibit TNF and inflammatory diseases, including inflammatory arthritis, are believed to involve TNF and NK-κB signaling. Therefore, dimethyl fumarate may be useful in treating inflammatory arthritis (Lowewe et al., *J Immunology* (2002), 168: 4781-4787).

The efficacy of the dimethyl fumarate cocrystals for treating inflammatory arthritis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied, with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* (2001), 81: 263-281; and Virley, *NeuroRx* (2005), 2(4): 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, any one of which negatively impacts the quality of life of the individual. The clinical course of MS can vary from individual to individual, but invariably the disease can be categorized in three forms: relapsing-remitting, secondary progressive, and primary progressive.

Studies support the efficacy of fumaric acid esters for treating MS and dimethyl fumarate has been approved in the US for such treatment (Schimrigk et al., *Eur J Neurology* (2006), 13: 604-610; and Wakkee and Thio, *Current Opinion Investigational Drugs* (2007), 8(11): 955-962).

Assessment of MS treatment efficacy in clinical trials can be accomplished using tools such as the Expanded Disability Status Scale and the MS Functional, as well as magnetic resonance imaging, lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

The efficacy of the dimethyl fumarate cocrystals for treating MS can be determined using animal models and in clinical trials.

Inflammatory Bowel Disease (Crohn's Disease, Ulcerative Colitis)

Inflammatory bowel disease (IBD) is a group of inflammatory conditions of the large intestine, and in some cases the small intestine, that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

Fumaric acid esters are inhibitors of NF-κB activation and therefore may be useful in treating inflammatory diseases such as Crohn's disease and ulcerative colitis (Atreya et al., *J Intern Med* (2008), 263(6): 591-596).

The efficacy of the dimethyl fumarate cocrystals for treating inflammatory bowel disease can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

As an inhibitor of NF-κB activation and as shown in animal studies (Joshi et al., U.S. Patent Application Publication No. 2007/0027076) fumaric acid esters may be useful in treating pulmonary diseases such as asthma and chronic obstructive pulmonary disorder.

The efficacy of the dimethyl fumarate cocrystals for treating asthma can be assessed using animal models and in clinical trials.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, *Pharmacological Reviews* (2004), 56(4): 515-548). The airflow limitation is usually progressive and associated with an abnormal inflammatory response of the lungs to noxious particles and gases. COPD is characterized by a shortness of breath that can last for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering the dimethyl fumarate cocrystals for treating chronic obstructive pulmonary disease may be assessed using animal models of chronic obstructive pulmonary disease and in clinical studies. For example, murine models of chronic obstructive pulmonary disease are known.

Neurodegenerative Disorders

Neurodegenerative diseases such as Parkinson's disease, Alzheimer's disease, Huntington's disease and amyoptrophic lateral sclerosis are characterized by progressive dysfunction and neuronal death. NF-κB inhibition has been proposed as a therapeutic target for neurodegenerative diseases (Camandola and Mattson, *Expert Opin Ther Targets* (2007), 11(2): 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia (e.g., the substantia nigra) degenerate, and thereby reduce the production of dopamine and the number of connections between nerve cells in the basal ganglia. As a result, the basal ganglia are unable to control smooth muscle movements and coordinate changes in posture as normal, leading to tremor, incoordination, and slowed, reduced movement (bradykinesia) (Blandini, et al., *Mol. Neurobiol.* (1996), 12: 73-94).

The efficacy of the dimethyl fumarate cocrystals for treating Parkinson's disease may be assessed using animal and human models of Parkinson's disease and in clinical studies.

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques (e.g., clumps of dead nerve cells containing an abnormal, insoluble protein called amyloid) and neurofibrillary tangles, twisted strands of insoluble proteins in the nerve cell.

The efficacy of the dimethyl fumarate cocrystals for treating Alzheimer's disease may be assessed using animal and human models of Alzheimer's disease and in clinical studies.

Huntington's Disease

Huntington's disease is an autosomal dominant neurodegenerative disorder in which specific cell death occurs in the neostriatum and cortex (Martin, *N Engl J Med* (1999), 340: 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

The efficacy of the dimethyl fumarate cocrystals for treating Huntington's disease may be assessed using animal and human models of Huntington's disease and in clinical studies.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, *N Engl J Med* (2001), 344: 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

The efficacy the dimethyl fumarate cocrystals for treating ALS may be assessed using animal and human models of ALS and in clinical studies.

Other Diseases

Other diseases and conditions for which the dimethyl fumarate cocrystals can be useful in treating include: rheumatica, granuloma annulare, lupus, autoimmune carditis, eczema, sarcoidosis, autoimmune diseases including acute disseminated encephalomyelitis, Addison's disease, alopecia areata, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, rheumatoid arthritis, schizophrena, scleroderma, Sjogren's syndrome, stiff person syndrome, temporal arteritis, ulcerative colitis, vasculitis, vitiligo, Wegener's granulomatosis, optic neuritis, neuromyelitis optica, subacute necrotizing myelopathy, balo concentric sclerosis, transverse myelitis, susac syndrome, central nervous system vasculitis, neurosarcoidosis, Charcott-Marie-Tooth Disease, progressive supranuclear palsy, neurodegeneration with brain iron accumulation, pareneoplastic syndromes, primary lateral sclerosis, Alper's Disease, monomelic myotrophy, adrenal leukodystrophy, Alexander's Disease, Canavan disease, childhood ataxia with central nervous system hypomyelination, Krabbe Disease, Pelizaeus-Merzbacher disease, Schilders Disease, Zellweger's syndrome, Sjorgren's Syndrome, human immunodeficiency viral infection, hepatitis C viral infection, herpes simplex viral infection and tumors.

EXAMPLES

Example 1

Synthesis, Purification and Analysis of Cocrystal of Dimethyl Fumarate and Gentisic Acid Cocrystals of dimethyl fumarate and gentisic acid were prepared as follows. 82.5 mg of dimethyl fumarate and 154.1 mg of gentisic acid were mixed with 1 ml of 1:3 (v:v) ethyl acetate:heptane. The mixture was sonicated for 5 min. and then stirred for 2 days. The starting concentrations of dimethyl fumarate and gentisic acid were chosen such that the thermodynamically stable solid phase at equilibrium is the cocrystal of dimethyl fumarate and gentisic acid. The crystalline material that formed was isolated by vacuum filtration, and dried to yield the dimethyl fumarate: gentisic acid (1:2) cocrystal. The measured melting points were 103±1° C. for dimethyl fumarate, 206±2° C. for gentisic acid, and 116±2° C. for the cocrystal.

Differential Scanning Calorimetry (DSC) Analysis

The DSC analysis was conducted using the TA Instruments Q2000 DSC equipped with a refrigerated cooling system. For all DSC analysis, 2-5 mg of sample was loaded into $T_{zero}$ aluminum pans with crimpled lids. A pinhole was made at the center of the lid to avoid any pressure buildup during heating. Samples were equilibrated at 10° C. and heated at a rate of 10° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 3) shows that the dimethyl fumarate:gentisic acid cocrystal first melts at about 116.54° C., which is significantly higher than the melting point of crystalline dimethyl fumarate. The melting points of dimethyl fumarate and gentisic acid are 103.16° C. and 206° C., respectively. The second melting transition with onset temperature at 205.89° C. corresponds roughly to the melting point of gentisic acid, which has a melting point of about 205° C.-207° C.

Thermogravimetric Analysis (TGA)

The thermal gravimetric analysis was conducted using a TA Instruments Q5000 thermogravimetric analyzer. For all TGA analysis, 5-10 mg of sample was loaded to a platinum pan and was heated to 250° C. at a rate of 10° C. per minute under a purge of dry nitrogen gas. The data acquisition was controlled by Thermal Advantage software Release 4.9.1. The data was analyzed with Universal Analysis 2000 software (version 4.5A).

Figure 12:
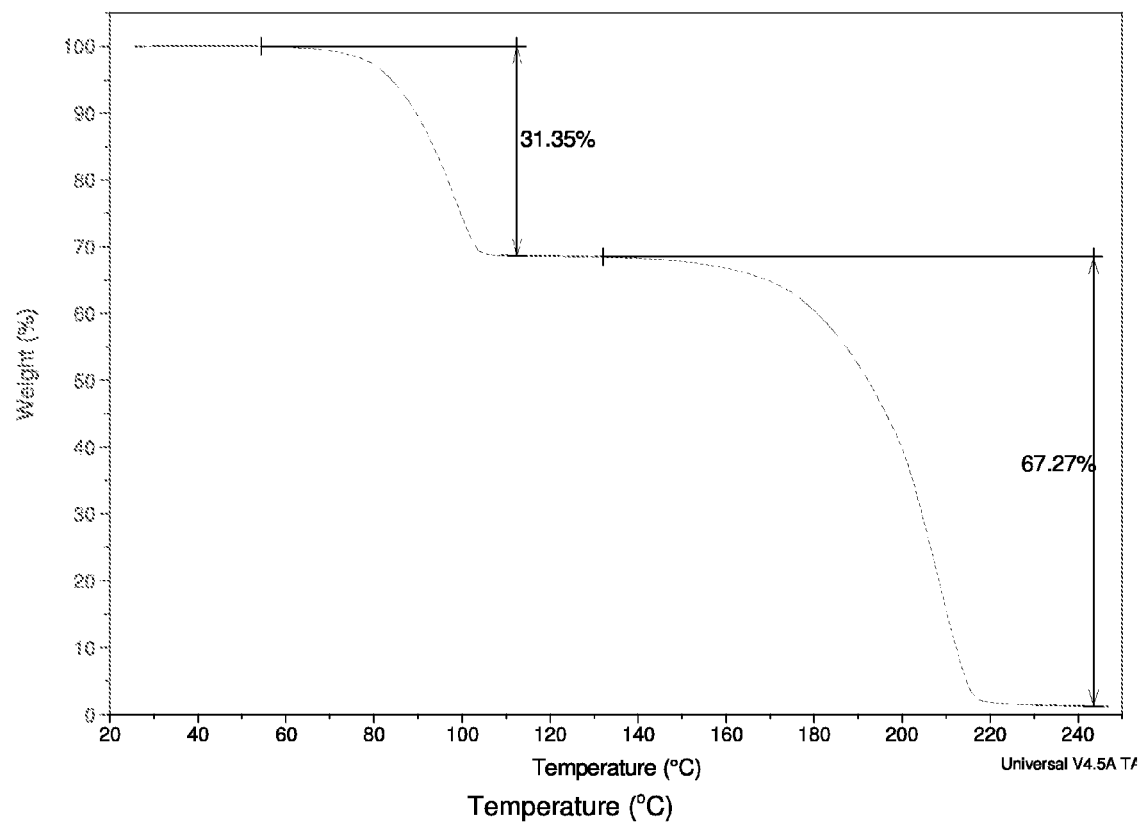
FIG. 12 is a thermogravimetric (TGA) thermogram, measured using an open pan, of a cocrystal of dimethyl fumarate and gentisic acid.

The TGA thermogram (FIG. 12) shows that the dimethyl fumarate:gentisic acid cocrystal undergoes weight loss prior to melting. The thermogram indicates that DMF sublimes from cocrystal lattice prior to melting under $N_2$ purge; and the 31.55% weight loss suggests the DMF:gentisic acid stoichiometric ratio of about 1:2.

X-ray Powder Diffraction (XRPD) Analysis

Powder X-ray diffraction analysis was performed using the PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for the dimethyl fumarate:gentisic acid cocrystal is shown in FIG. 1. Unless otherwise specified, the experimental data for X-ray powder diffraction were collected at room temperature.

NMR Analysis

Proton NMR (400 MHz) NMR spectra were recorded on a Varian AS 400 NMR spectrometer equipped with an auto-sampler and data processing software. MeOH-$d_3$ (99.8+% D) was used as solvents unless otherwise noted. The MeOH-$d_3$ solvent signals were used for calibration of the individual spectra. The NMR spectral pattern for the dimethyl fumarate:gentisic acid cocrystal is shown in FIG. 2.

Example 2

Synthesis, Purification and Analysis of Cocrystal of Dimethyl Fumarate and (+)-Camphoric Acid Form 1

Cocrystals of dimethyl fumarate and (+)-camphoric acid were prepared as follows. 150 mg of dimethyl fumarate and 225 mg of (+)-camphoric acid were dissolved in 3 ml of ethyl acetate with stirring and gentle heating. The clear solution was cooled to room temperature, and 9 ml of heptane were added. The unstirred solution was allowed to stand for 24 hours. The starting concentrations of dimethyl fumarate and (+)-camphoric acid were chosen such that the thermodynamically stable solid phase at equilibrium is the cocrystal of dimethyl fumarate and (+)-camphoric acid. The crystalline material that formed was isolated by vacuum filtration, and dried to yield the dimethyl fumarate: (+)-camphoric acid (1:16, by NMR) cocrystal form 1 (112 mg).

Differential Scanning Calorimetry (DSC) Analysis

DSC data were obtained using a TA Instruments differential scanning calorimeter 2920 equipped with a refrigerated cooling system. For all DSC analysis, 2-10 mg of sample was placed into an aluminum DSC pan, and the weight accurately recorded. The samples were run with open pans as well as in crimped pans (no pinhole). The sample cell heated at a rate of 10° C./min, up to a final temperature of 250° C. Indium metal was used as the calibration standard. The data acquisition was controlled by Thermal Advantage software Release 4.9.1. The data were analyzed with Universal Analysis 2000 software (version 4.5A).

DSC thermogram of the dimethyl fumarate:(+)-camphoric acid form 1 is shown in FIG. 6 and FIG. 7.

Thermogravimetric Analysis (TGA)

TGA data were obtained using a TA Instruments 2950 thermogravimetric analyzer. For all TGA analysis, 5-10 mg of sample was placed in an aluminum sample pan and inserted into the TGA furnace. The furnace was heated under nitrogen at a rate of 10° C./min, up to a final temperature of 250° C. Nickel and Alumel were used as the calibration standards.

X-ray Powder Diffraction (XRPD) Analysis

Data were collected on a Scintag X1 powder diffractometer equipped with a peltier cooled solid state detector. Data were collected between 2.5° and 40° 2-theta using a 0.05° step size and 25 minute total run time. Data were collected using Cu—$K_\alpha$ radiation and the tube voltage and amperage were set to 45 kV and 40 mA, respectively. Instrument calibration was performed using a quartz reference standard.

The X-ray diffraction pattern for the dimethyl fumarate:(+)-camphoric acid cocrystal form 1 is shown in FIG. 4. Unless otherwise specified, the experimental data for X-ray powder diffraction were collected at room temperature.

NMR Analysis $^1$H NMR spectra were acquired on a Varian INOVA 400 MHz instrument at 25° C., reported in ppm (δ) and referenced to DMSO-$d_6$ peak (2.50 ppm). The spectra were processed in MestReNova version 6.2.1. Water was present in the DMSO-d6 used to prepare the samples and this broad peak is located at 3.42 ppm.

The NMR spectral pattern for the dimethyl fumarate:(+)-camphoric acid cocrystal form 1 is shown in FIG. 5.

Example 3

Synthesis, Purification and Analysis of Cocrystal of Dimethyl Fumarate and (+)-Camphoric Acid Form 2

Cocrystals of dimethyl fumarate and (+)-camphoric acid were prepared as follows. 36 mg of dimethyl fumarate and 200 mg of (+)-camphoric acid were combined in an agate jar with a 4 ml capacity. One drop of 1:3 (v:v) ethyl acetate:heptane was added along with two agate grinding balls. The mixture was milled for 60 minutes at full power on a Retch mm2 mixer mill. The starting concentrations of dimethyl fumarate and (+)-camphoric acid were chosen such that the thermodynamically stable solid phase at equilibrium is the cocrystal of dimethyl fumarate and (+)-camphoric acid. The crystalline material that formed was isolated to yield the dimethyl fumarate: (+)-camphoric acid (1:4, by NMR) cocrystal. The measured melting points were 103±1° C. for dimethyl fumarate, 185±2° C. for (+)-camphoric acid, and 88±2° C. for the cocrystal.

Differential Scanning Calorimetry (DSC) Analysis

DSC data were obtained using a TA Instruments differential scanning calorimeter 2920. The sample was placed into an aluminum DSC pan, and the weight accurately recorded. The samples were run with open pans as well as in crimped pans (no pinhole). The sample cell heated at a rate of 10° C./min, up to a final temperature of 250° C. Indium metal was used as the calibration standard.

DSC thermogram of the dimethyl fumarate:(+)-camphoric acid form 2 is shown in FIG. 10 and FIG. 11.

Thermogravimetric Analysis (TGA)

TGA data were obtained using a TA Instruments 2950 thermogravimetric analyzer. Each sample was placed in an aluminum sample pan and inserted into the TGA furnace. The furnace was heated under nitrogen at a rate of 10° C./min, up to a final temperature of 250° C. Nickel and Alumel were used as the calibration standards.

Figure 13:
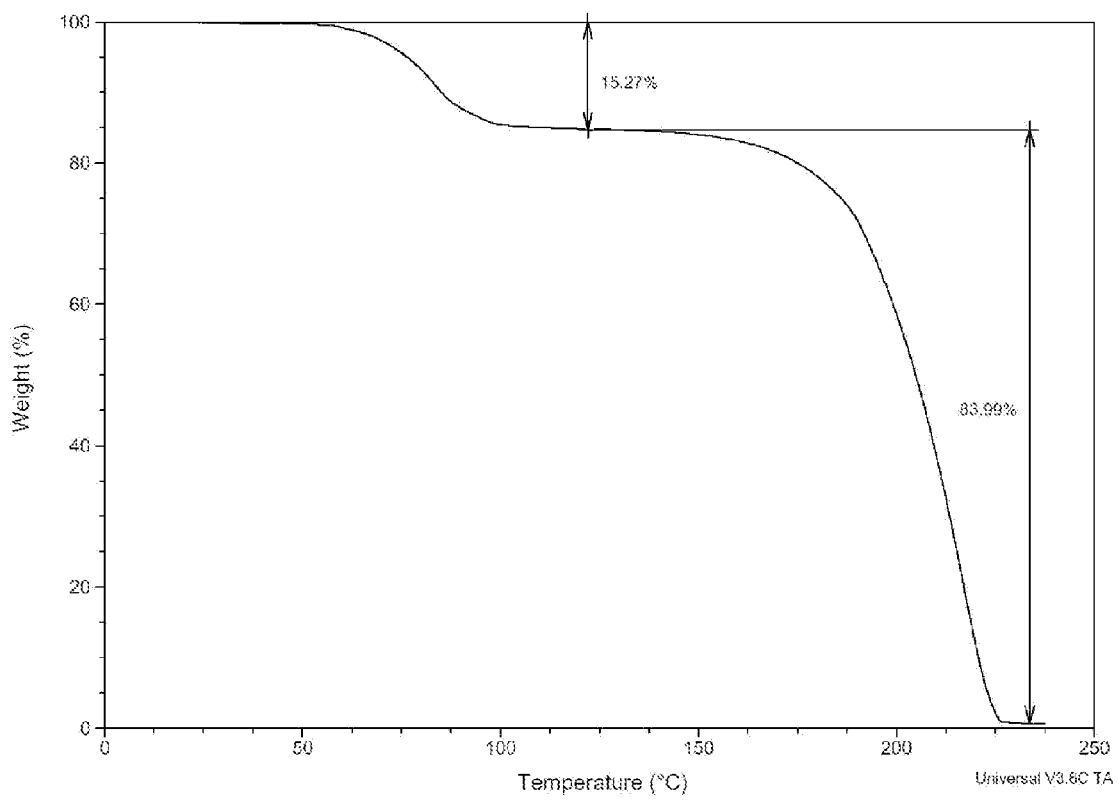
FIG. 13 is a thermogravimetric (TGA) thermogram, measured using an open pan, of a cocrystal of dimethyl fumarate and (+)-camphoric acid form 2, isolated from milling.

The TGA thermogram (FIG. 13) shows that the dimethyl fumarate:(+)-camphoric acid cocrystal form 2 undergoes weight loss prior to melting, The thermogram indicates that DMF sublimes from cocrystal lattice; and the 15.27% weight loss suggests the DMF:(+)-camphoric acid stoichiometric ratio of about 1:4.

X-ray Powder Diffraction (XRPD) Analysis

Data were collected on a Scintag X1 powder diffractometer equipped with a peltier cooled solid state detector. Data were collected between 2.5° and 40° 2-theta using a 0.05° step size and 25 minute total run time. Data were collected using Cu—$K_\alpha$ radiation and the tube voltage and amperage were set to 45 kV and 40 mA, respectively. Instrument calibration was performed using a quartz reference standard. All data described herein are in copper wavelength.

The X-ray diffraction pattern for the dimethyl fumarate:(+)-camphoric acid cocrystal form 2 is shown in FIG. 8. Unless otherwise specified, the experimental data for X-ray powder diffraction were collected at room temperature.

NMR Analysis $^1$H NMR spectra were acquired on a Varian INOVA 400 MHz instrument at 25° C., reported in ppm (δ) and referenced to DMSO-d6 peak (2.50 ppm). The spectra were processed in MestReNova version 6.2.1. Water was present in the DMSO-d6 used to prepare the samples and this broad peak is located at 3.42 ppm.

The NMR spectral pattern for the dimethyl fumarate:(+)-camphoric acid form 2 cocrystal is shown in FIG. 9.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the embodiments disclosed herein. Accordingly, the above description should not be taken as limiting the scope of the document.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

The invention claimed is:

1. A cocrystal of dimethyl fumarate and gentisic acid.

2. The cocrystal of claim 1, having a molar ratio of dimethyl fumarate to gentisic acid of about 1:2.

3. The cocrystal of claim 1, having a DSC thermogram peak between about 114° C. and about 118° C.

4. The cocrystal of claim 1, which exhibits a characteristic scattering angle (2θ) at least at 13.0±0.2° in an X-ray powder diffractogram measured using Cu—$K_\alpha$ radiation.

5. The cocrystal of claim 4, which exhibits characteristic scattering angles (2θ) at least at 13.0±0.2°, 12.0±0.2°, 21.8±0.2°, 23.8±0.2°, and 27.7±0.2° in an X-ray powder diffraction pattern measured using Cu—$K_\alpha$ radiation.

6. The cocrystal of claim 5, which exhibits characteristic scattering angles (2θ) at least at 13.0±0.2°, 12.0±0.2°, 21.8±0.2°, 23.8±0.2°, 27.7±0.2°, 16.8±0.2°, 36.5±0.2°, 8.0±0.2°, 26.1±0.2° and 15.9±0.2° in an X-ray powder diffraction pattern measured using Cu—$K_\alpha$ radiation.

7. The cocrystal of claim 6, which exhibits characteristic scattering angles (2θ) at least at 13.0±0.2°, 12.0±0.2°, 21.8±0.2°, 23.8±0.2°, 27.7±0.2°, 16.8±0.2°, 36.5±0.2°, 8.0±0.2°, 26.1±0.2°, 15.9±0.2°, 23.4±0.2°, 24.4±0.2°, 23.0±0.2°, 31.9±0.2°, 20.7±0.2°, and 29.6±0.2° in an X-ray powder diffraction pattern measured using Cu—$K_\alpha$ radiation.

8. The cocrystal of any one of claim 1, which exhibits an X-ray powder diffraction pattern that is substantially same as FIG. 1.

9. A pharmaceutical composition comprising a cocrystal according to claim 1 and a pharmaceutically acceptable carrier.

10. A method of treating a disease in a patient in need of such treatment, the disease selected from multiple sclerosis and psoriasis, comprising administering to the patient a therapeutically effective amount of a cocrystal according to claim 1.

* * * * *